United States Patent
Wong

(10) Patent No.: US 9,592,242 B2
(45) Date of Patent: *Mar. 14, 2017

(54) METHODS FOR TREATING EDEMA IN THE EYE AND INTRAOCULAR IMPLANTS FOR USE THEREFOR

(71) Applicant: Allergan, Inc., Irvine, CA (US)

(72) Inventor: Vernon G. Wong, Menlo Park, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/069,584

(22) Filed: Mar. 14, 2016

(65) Prior Publication Data

US 2016/0193230 A1 Jul. 7, 2016

Related U.S. Application Data

(60) Continuation of application No. 14/481,778, filed on Sep. 9, 2014, now Pat. No. 9,283,178, which is a continuation of application No. 13/871,214, filed on Apr. 26, 2013, now Pat. No. 8,828,446, which is a continuation of application No. 13/296,957, filed on Nov. 15, 2011, now abandoned, which is a continuation of application No. 11/852,223, filed on Sep. 7, 2007, now Pat. No. 8,088,407, which is a division of application No. 11/738,409, filed on Apr. 20, 2007, now Pat. No. 7,625,582, which is a division of application No. 11/180,079, filed on Jul. 11, 2005, now Pat. No. 7,767,223, which is a continuation of application No. 10/744,560, filed on Dec. 22, 2003, now Pat. No. 7,033,605, which is a continuation of application No. 09/997,094, filed on Nov. 28, 2001, now Pat. No. 6,699,493.

(60) Provisional application No. 60/250,023, filed on Nov. 29, 2000, provisional application No. 60/298,253, filed on Jun. 12, 2001.

(51) Int. Cl.

| | | |
|---|---|---|
| A61F 2/14 | (2006.01) |
| A61K 31/573 | (2006.01) |
| A61F 9/00 | (2006.01) |
| A61K 9/00 | (2006.01) |
| A61K 9/16 | (2006.01) |
| A61K 31/56 | (2006.01) |
| A61K 31/715 | (2006.01) |
| A61K 31/765 | (2006.01) |
| A61K 45/06 | (2006.01) |
| A61L 27/54 | (2006.01) |
| A61K 47/34 | (2006.01) |

(52) U.S. Cl.
CPC .......... *A61K 31/573* (2013.01); *A61F 9/0008* (2013.01); *A61F 9/0017* (2013.01); *A61K 9/0048* (2013.01); *A61K 9/0051* (2013.01); *A61K 9/1641* (2013.01); *A61K 9/1647* (2013.01); *A61K 31/56* (2013.01); *A61K 31/715* (2013.01); *A61K 31/765* (2013.01); *A61K 45/06* (2013.01); *A61K 47/34* (2013.01); *A61L 27/54* (2013.01); *A61F 2210/0004* (2013.01); *A61L 2300/222* (2013.01); *A61L 2300/41* (2013.01); *A61L 2300/416* (2013.01); *A61L 2300/604* (2013.01)

(58) Field of Classification Search
CPC .. A61K 9/0051; A61K 9/1647; A61K 31/573; A61F 9/00171
See application file for complete search history.

(56) References Cited

U.S. PATENT DOCUMENTS

| | | |
|---|---|---|
| 3,416,530 A | 12/1968 | Ness |
| 3,432,592 A | 3/1969 | Speiser |
| 3,845,770 A | 11/1974 | Theeuwes et al. |
| 3,914,402 A | 10/1975 | Shell |
| 3,916,899 A | 11/1975 | Theeuwes et al. |
| 3,921,632 A | 11/1975 | Bardani |
| 3,961,628 A | 6/1976 | Arnold |
| 3,986,510 A | 10/1976 | Higuchi et al. |
| 4,008,864 A | 2/1977 | Torphammar et al. |
| 4,014,334 A | 3/1977 | Theeuwes et al. |
| 4,063,064 A | 12/1977 | Saunders et al. |
| 4,088,864 A | 5/1978 | Theeuwes et al. |
| 4,144,317 A | 3/1979 | Higuchi et al. |
| 4,180,646 A | 12/1979 | Choi et al. |
| 4,186,184 A | 1/1980 | Zaffaroni |
| 4,200,098 A | 4/1980 | Ayer et al. |
| 4,201,210 A | 5/1980 | Hughes et al. |

(Continued)

FOREIGN PATENT DOCUMENTS

| | | |
|---|---|---|
| CA | 1333770 | 1/1995 |
| CA | 2336703 | 1/2000 |
| EA | 0430538 A1 | 6/1991 |
| EP | 0052916 | 7/1981 |
| EP | 0102265 | 3/1984 |
| EP | 0197718 | 10/1986 |
| EP | 0311065 | 10/1988 |
| EP | 0364417 | 9/1989 |
| EP | 0474098 | 3/1992 |
| EP | 0488401 | 6/1992 |

(Continued)

OTHER PUBLICATIONS

Aguilar, Edith et al, Vancomycin Levels After Intravitreal Injection: Effects of Inflammation and Surgery, Retina, 1995, 428-432, 15.

(Continued)

*Primary Examiner* — Carlos Azpuru
(74) *Attorney, Agent, or Firm* — Laura L. Wine

(57) ABSTRACT

Methods for reducing or preventing transplant rejection in the eye of an individual are described, comprising: a) performing an ocular transplant procedure; and b) implanting in the eye a bioerodible drug delivery system comprising an immunosuppressive agent and a bioerodible polymer.

6 Claims, No Drawings

(56) References Cited

U.S. PATENT DOCUMENTS

| | | |
|---|---|---|
| 4,285,987 A | 8/1981 | Ayer et al. |
| 4,300,557 A | 11/1981 | Refojo et al. |
| 4,304,765 A | 12/1981 | Shell et al. |
| 4,327,725 A | 5/1982 | Cortese |
| 4,402,979 A | 9/1983 | Shen et al. |
| 4,451,254 A | 5/1984 | Dinius et al. |
| 4,474,451 A | 10/1984 | Mizokami |
| 4,478,818 A | 10/1984 | Shell et al. |
| 4,494,274 A | 1/1985 | Thurlow |
| 4,521,210 A | 6/1985 | Wong |
| 4,599,353 A | 7/1986 | Bito |
| 4,668,506 A | 5/1987 | Bawa |
| 4,756,911 A | 7/1988 | Drost |
| 4,801,460 A | 1/1989 | Goertz et al. |
| 4,806,337 A | 2/1989 | Snipes et al. |
| 4,853,224 A | 8/1989 | Wong |
| 4,863,457 A | 9/1989 | Lee |
| 4,865,846 A | 9/1989 | Kaufman |
| 4,945,089 A | 7/1990 | Clark |
| 4,959,217 A | 9/1990 | Sanders et al. |
| 4,966,849 A | 10/1990 | Vallee et al. |
| 4,997,652 A | 3/1991 | Wong |
| 5,004,601 A | 4/1991 | Snipes |
| 5,004,614 A | 4/1991 | Staniforth |
| 5,006,342 A | 4/1991 | Cleary et al. |
| 5,019,400 A | 5/1991 | Gombotz et al. |
| 5,028,624 A | 7/1991 | Chan et al. |
| 5,034,413 A | 7/1991 | Chan et al. |
| 5,075,115 A | 12/1991 | Brine |
| 5,082,655 A | 1/1992 | Snipes et al. |
| 5,164,188 A | 11/1992 | Wong |
| 5,169,638 A | 12/1992 | Dennis et al. |
| 5,268,178 A | 12/1993 | Calhoun et al. |
| 5,314,419 A | 5/1994 | Pelling |
| 5,322,691 A | 6/1994 | Darougar et al. |
| 5,330,992 A | 7/1994 | Eissenstat et al. |
| 5,356,629 A | 10/1994 | Sander et al. |
| 5,378,475 A | 1/1995 | Smith |
| 5,384,333 A | 1/1995 | Davis et al. |
| 5,385,887 A | 1/1995 | Yim et al. |
| 5,443,505 A | 8/1995 | Wong et al. |
| 5,476,511 A | 12/1995 | Gwon et al. |
| 5,501,856 A | 3/1996 | Ohtori et al. |
| 5,597,897 A | 1/1997 | Ron et al. |
| 5,601,844 A | 2/1997 | Kagayama et al. |
| 5,656,297 A | 8/1997 | Berstein et al. |
| 5,660,847 A | 8/1997 | Magruder et al. |
| 5,660,851 A | 8/1997 | Domb |
| 5,688,819 A | 11/1997 | Woodward et al. |
| 5,693,335 A | 12/1997 | Xia et al. |
| 5,707,643 A | 1/1998 | Ogura |
| 5,755,785 A | 5/1998 | Rowsey et al. |
| 5,766,242 A | 6/1998 | Wong et al. |
| 5,773,019 A | 6/1998 | Ashton et al. |
| 5,773,021 A | 6/1998 | Gurtler et al. |
| 5,824,072 A | 10/1998 | Wong |
| 5,824,074 A | 10/1998 | Koch |
| 5,869,079 A | 2/1999 | Wong et al. |
| 5,882,682 A | 3/1999 | Rork et al. |
| 5,902,598 A | 5/1999 | Chen et al. |
| 5,941,250 A | 8/1999 | Aramant et al. |
| 5,962,027 A | 10/1999 | Hughes |
| 5,972,369 A | 10/1999 | Roorda et al. |
| 6,045,791 A | 4/2000 | Liu |
| 6,046,187 A | 4/2000 | Berde et al. |
| 6,051,576 A | 4/2000 | Ashton et al. |
| 6,063,116 A | 5/2000 | Kelleher |
| 6,074,661 A | 6/2000 | Olejnik et al. |
| 6,217,895 B1 | 4/2001 | Guo et al. |
| 6,217,911 B1 | 4/2001 | Vaugn et al. |
| 6,306,426 B1 | 10/2001 | Olejnik et al. |
| 6,309,669 B1 | 10/2001 | Setterstrom et al. |
| 6,329,369 B1 | 12/2001 | Chow |
| 6,331,313 B1 | 12/2001 | Wong et al. |
| 6,369,116 B1 | 4/2002 | Wong et al. |
| 6,403,649 B1 | 6/2002 | Woodward |
| 6,497,729 B1 | 12/2002 | Moussy et al. |
| 6,534,542 B2 | 3/2003 | Chow et al. |
| 6,537,568 B2 | 3/2003 | Olejnik et al. |
| 6,545,182 B2 | 4/2003 | Chow et al. |
| 6,548,078 B2 | 4/2003 | Guo et al. |
| 6,699,493 B2 | 3/2004 | Wong |
| 6,699,495 B2 | 3/2004 | Blume et al. |
| 6,713,081 B2 | 3/2004 | Robinson et al. |
| 6,726,918 B1 | 4/2004 | Wong et al. |
| 6,841,684 B2 | 1/2005 | Chow |
| 6,899,717 B2 | 5/2005 | Lathrop et al. |
| 7,033,605 B2 | 4/2006 | Wong |
| 7,048,946 B1 | 5/2006 | Wong |
| 7,090,681 B2 | 8/2006 | Weber et al. |
| 7,091,232 B2 | 8/2006 | Chow |
| 7,141,597 B2 | 11/2006 | Chow et al. |
| 7,147,644 B2 | 12/2006 | Weber et al. |
| 7,276,522 B2 | 10/2007 | Heidelbaugh et al. |
| 7,282,216 B2 | 10/2007 | Costantino et al. |
| 7,335,803 B2 | 2/2008 | Chow et al. |
| 7,468,065 B2 | 12/2008 | Weber et al. |
| 7,625,582 B2 | 12/2009 | Wong et al. |
| 7,675,582 B2 | 3/2010 | Luo et al. |
| 7,753,916 B2 | 7/2010 | Weber et al. |
| 7,767,223 B2 | 8/2010 | Wong |
| 7,846,468 B2 | 12/2010 | Wong |
| 8,034,366 B2 | 10/2011 | Shiah |
| 8,034,370 B2 | 10/2011 | Shiah |
| 8,043,628 B2 * | 10/2011 | Wong .................... A61F 9/0008 424/428 |
| 8,048,445 B2 | 11/2011 | Shiah et al. |
| 8,063,031 B2 | 11/2011 | Wong et al. |
| 8,071,120 B2 | 12/2011 | Wong et al. |
| 8,088,407 B2 * | 1/2012 | Wong .................... A61F 9/0008 424/428 |
| 8,119,154 B2 | 2/2012 | Huang et al. |
| 8,242,099 B2 | 8/2012 | Wong et al. |
| 8,318,070 B2 | 11/2012 | Shiah et al. |
| 9,283,178 B2 * | 3/2016 | Wong .................... A61F 9/0008 |
| 2001/0053370 A1 | 12/2001 | Donovan |
| 2002/0111603 A1 | 8/2002 | Cheikh |
| 2003/0007992 A1 | 1/2003 | Gibson et al. |
| 2003/0069560 A1 | 4/2003 | Adamis et al. |
| 2004/0019098 A1 | 1/2004 | Andrews et al. |
| 2004/0057979 A1 | 3/2004 | Wong et al. |
| 2004/0127843 A1 | 7/2004 | Tu et al. |
| 2004/0132824 A1 | 7/2004 | Gil et al. |
| 2004/0137059 A1 | 7/2004 | Nivaggioli et al. |
| 2004/0151753 A1 | 8/2004 | Chen et al. |
| 2004/0170665 A1 | 9/2004 | Donovan |
| 2004/0208910 A1 | 10/2004 | Ashton et al. |
| 2004/0266776 A1 | 12/2004 | Gil et al. |
| 2005/0048099 A1 | 3/2005 | Shiah et al. |
| 2005/0058696 A1 | 3/2005 | Donello et al. |
| 2005/0059664 A1 | 3/2005 | Gil et al. |
| 2005/0059744 A1 | 3/2005 | Donello et al. |
| 2005/0101582 A1 | 5/2005 | Lyons et al. |
| 2005/0181017 A1 | 8/2005 | Hughes et al. |
| 2005/0232966 A1 | 10/2005 | Hughes et al. |
| 2005/0244464 A1 | 11/2005 | Hughes |
| 2005/0244467 A1 | 11/2005 | Nivaggioli et al. |
| 2005/0244469 A1 | 11/2005 | Whitcup et al. |
| 2005/0244474 A1 | 11/2005 | Huang et al. |
| 2006/0009498 A1 | 1/2006 | Whitcup |
| 2006/0198871 A1 | 9/2006 | Wong |
| 2006/0233857 A1 | 10/2006 | Amsden et al. |
| 2006/0233859 A1 | 10/2006 | Whitcup et al. |
| 2007/0224246 A1 | 9/2007 | Hughes et al. |
| 2007/0298073 A1 | 12/2007 | Whitcup et al. |
| 2007/0298076 A1 | 12/2007 | Wong et al. |
| 2008/0050420 A1 | 2/2008 | Wong |
| 2008/0050421 A1 | 2/2008 | Wong |
| 2008/0069859 A1 | 3/2008 | Wong |
| 2008/0107712 A1 | 5/2008 | Shiah et al. |
| 2008/0241223 A1 | 10/2008 | Nivaggioli et al. |
| 2008/0286334 A1 | 11/2008 | Shiah et al. |
| 2008/0286336 A1 | 11/2008 | Shiah et al. |
| 2009/0082863 A1 | 3/2009 | Schieber et al. |

(56) References Cited

U.S. PATENT DOCUMENTS

| | | |
|---|---|---|
| 2011/0091520 A1 | 4/2011 | Huang |
| 2011/0305743 A1 | 12/2011 | Shiah et al. |
| 2012/0059462 A1 | 3/2012 | Wong |
| 2012/0114734 A1 | 5/2012 | Desai et al. |
| 2012/0252771 A1 | 10/2012 | Wong et al. |

FOREIGN PATENT DOCUMENTS

| | | |
|---|---|---|
| EP | 0322319 | 8/1992 |
| EP | 0430539 | 10/1994 |
| EP | 0654256 | 5/1995 |
| EP | 0992244 | 4/2000 |
| EP | 1550471 | 7/2005 |
| WO | 91-15495 | 10/1991 |
| WO | 91-18940 | 12/1991 |
| WO | 92-21660 | 12/1992 |
| WO | 93-10141 | 9/1993 |
| WO | 94-03427 | 2/1994 |
| WO | 94-10202 | 5/1994 |
| WO | 94-14808 | 7/1994 |
| WO | 94-18956 | 9/1994 |
| WO | 95-13765 | 5/1995 |
| WO | 96-38174 | 12/1996 |
| WO | 97-26869 | 7/1997 |
| WO | 98-22130 | 5/1998 |
| WO | 99-11244 | 3/1999 |
| WO | 00-02564 | 1/2000 |
| WO | 00-13717 | 3/2000 |
| WO | 00-37056 | 6/2000 |
| WO | 00-56340 | 9/2000 |
| WO | 00-62760 | 10/2000 |
| WO | 01-30323 | 5/2001 |
| WO | 01-21173 | 7/2001 |
| WO | 02-02076 | 1/2002 |
| WO | 02-43785 | 6/2002 |
| WO | 03-094888 | 11/2003 |
| WO | 2004-026106 | 4/2004 |
| WO | 2004-062649 | 7/2004 |
| WO | 2005-107705 | 11/2005 |
| WO | 2005-110362 | 11/2005 |
| WO | 2005-110366 | 11/2005 |
| WO | 2005-110380 | 11/2005 |
| WO | 2006-036280 | 4/2006 |
| WO | 2006-093758 | 9/2006 |
| WO | 2007-130945 | 11/2007 |

OTHER PUBLICATIONS

Ahmad, M. et al, Ortho Ester Hydrolysis: Direct Evidence for a Three-Stage Reaction Mechanism, American Chemical Society, May 9, 1979, 2669-2677.
Ahmed, Irma et al, 34: Cystoid Macular Edema, 1999, 34.1-34.6.
Akduman, Levent et al, The Early Treatment Diabetic Retinopathy Study, Clinical Trials in Ophthalmology, 1998, 15-35.
Algvere, Peep et al, Transplantation of RPE in Age-Related Macular Degeneration: Observations in Discriform Lesions and Dry RPE Atrophy, Graefe's Arch Clin Exp Ophthalmol, 1997, 149-158, 235.
Anderson, Lynne et al, An Injectable Sustained Release Fertility Control System, Contraception, 1976, 375-384, 13.
Andreau, Karine et al, Induction of Apoptosis by Dexamethasone in the B Cell Lineage, Immunopharmacology, 1998, 67-76, 40.
Antcliff, R.J. et al, The Pathogenesis of Edema in Diabetic Maculopathy, Seminars in Ophthalmology, Dec. 1999, 223-232, 14(4).
Apel, Andrew, A Subconjunctival Degradable Implant for Cyclosporine Delivery in Corneal Transplant Therapy, current Eye Research, Apr. 3, 1995, 659-667, Oxford University Press, US.
Araie, M. et al, The Loss of Fluorescein, Fluorescein Glucuronide and Fluorescein Isothiocyanate Dextran From the Vitreous by the Anterior and Retinal Pathways, Exp. Eye Res., 1991, 27-39, 52.
Baker, Richard, Controlled Release of Biologically Active Agent, A Wiley, 1987, 73-75, Interscience Publication.

Barnas, U. et al, Parameters Associated with Chronic Renal Transplant Failure, Nephrol Dial Transplant, 1997, 82-85, 12(Suppl. 2).
Barza, Michael et al, Pharmacokinetics of Intravitreal Carbenicillin, Cefazolin, and Gentamicin in Rhesus Monkeys, Invest. Ophthalmol. Vis. Sci., 1983, 1602-1606, 24.
Beck, Roy et al, A Randomized, Controlled Trial of Corticosteroids in the Treatment of Acute Optic Neuritis, The New England Journal of Medicine, Feb. 27, 1992, 581-588, 326 (9).
Beck, Roy et al, The Effect of Corticosteroids for Acute Optic Neuritis on the Subsequent Development of Multiple Sclerosis, The New England journal of Medicine, Dec. 9, 1993, 1764-1769, 329 (24).
Beeley, Nathan et al, Fabrication, Implantation, Elution, and Retrival of a Steroid-Loaded Polycaprolactone Subretinal Implant, Journal of Biomedical Materials Research, Jun. 15, 2005, 437-444, 73 (4).
Ben-Nun, J. et al, Pharmacokinetics of Intravitreal Injection, Investigative Ophthalmology & Visual Science, Jun. 1989, 1055-1061, 30(6).
Bennett, William et al, Failure of Dexamethasone to Provide Adequate Chronic Immunosuppression for Renal Transplantation, Official Journal of the Transplantation Society, Mar. 1979, 218-219, 27(3).
Bigar, Francis et al, Corneal Transplantation, Opinion in Ophthalmology, 1992, 473-481, 3(4).
Bingaman, D.R et al, Inhibition of Preretinal Neovascularization in Pigs by Intravitreal Triamcinolone Acetonide, Investigative Ophthalmology & Visual Science, Mar. 15, 1995, S401, 36(4).
Bito, LZ, Biological Protection with Prostanoids, CRC Press, Inc., 1985, 231-252, 1, Cohen, M. M., ed., Boca Raton, Fla.
Bito, LZ, Prostaglandins, Old Concepts and New Perspectives, Archives of Ophthalmology, 1987, 1036-1039, 105.
Bito, LZ, Prostaglandins, Other Eicosanoids, and Their derivatives as Potential Antiglaucoma Agents, Glaucoma: Applied Pharmacology, 1984, 477-505, 20.
Bloch-Michel, Etienne, Opening Address: Intermediate Uveitis, Dev. Ophthalmol., 1992, 1-2, 23.
Bodor, Nicholas et al, A Comparison of Intraocular Pressure Elevating Activity of Loteprednoletabonate and Dexamethasone in Rabbits, Current Eye Research, 1992, 525-530, 11.
Boke, Kiel et al, Clinical Picture of Intermediate Uveitis, International Workshop on Intermediate Uveitis, 1992, 20-27, 23.
Bolen, Joseph, Nonreceptor Tyrosine Protein Kinases, Oncogene, 1993, 2025-2031, 8.
Brubaker, Richard, Mechanism of Action of Bimatoprost (LumiganTM), Sury Ophthalmol, 2001, S347-S351, 45-Suppl 4.
Budavari, Susan et al, The Merck Index, 1997, 12th Edition, 3 Pages.
Bundgaard, Hans et al, Prodrugs of Peptides IV: Bioreversible Derivatization of the Pyroglutamyl Group by N-Acylation and N-Aminomethylation to Effect Protection Against Pyroglutamyl Aminopeptidase, Journal of Pharmaceutical Sciences, Feb. 1989, 122-126, 78(2).
Burdon, Michael et al, A Survey of Corneal Graft Practice in the United Kingdom, Eye, 1995, 6-12, 9.
Carolyn H. Kwak, Botulinum Toxin in the Treatment of Tics, 2000.
Chacko, David et al, Survival and Differentiation of Cultured Retinal Progenitors Transplanted in the Subretinal Space of the Rat, Biochemical and Biophysical Research Communications, 2000, 842-846, 268.
Challa, Jagannadh et al, Exudative Macular Degeneration and Intravitreal Triamcinolone: 18 Month Follow Up, Australian and New Zealand Journal of Ophthalmology, 1998, 277-281, 26.
Chang, David et al, Phase II Results of an Intraocular Steroid Delivery System for Cataract Surgery, Ophthalmology, 1999, 1172-1177, 106.
Chang, Mary et al, Basic Science and Clinical Aspects of Wound Healing in Glaucoma Filtering Surgery, Journal of Ocular Pharmacology and Therapeutics, 1998, 75-95, 14(1).
Charles, Jean-Bernard et al, Use of Bioerodible Polymers Impregnated with Mitomycin in Glaucoma Filtration Surgery in Rabbits, Ophthalmology, Apr. 1991, 503-508, 98-4.

(56) References Cited

OTHER PUBLICATIONS

Chen, June et al, LumiganR: A Novel Drug for Glaucoma Therapy, Optom in Pract., Jun. 12, 2002, 95-102, 3.

Cheng, Cheng-Kuo et al, Intravitreal Sustained-Release Dexamethasone Device in the Treatment of Experimental Uveites, Investigative Ophthalmology & Visual Science, 1995, 442-453, 96 (2), US.

Clarkson, John, Central Retinal Vein Occlusion, Retinal Vascular Diseases, 1999, 1368-1375.

Coleman, Anne et al, A 3-Month Randomized Controlled Trial of Bimatoprost (LUMIGAN) Versus Combined Timolol and Dorzolamide (Cosopt) in Patients with Glaucoma or Ocular Hypertension, Ophthalmology, 2003, 2362-8, 110-12.

Cuff, George, et al, A Preliminary Evaluation of Injection Molding as a Technology to Produce Tablets, Advanstar Publication, 1998, 96-106, US.

Dabrowski, E. et. al., Botulinum Toxin as a Novel Treatment for Self Mutilation in Lesch-Nyhan Syndrome, Developmental Medicine & Child Neurology, 2005, 2 pages, 47 (9), US.

David F. Chang, et al, Two Clinical Trials of an Intraocular Steroid Delivery System for Cataract Surgery, Transaction of the American Ophthalmology Society, 1999, 261-279, 97, US.

Davis, P. A. et al, Intraocular Implant for Controlled 5-Fluorouracil Release, Procced. Intern. Symp. Control. Rel. Bioact. Mater, 1992, 339-340, US.

De Jong et al, New insights into the hydrolytic degradation of poly(lactic acid): participation of the alcohol terminus, Polymer, 2001, 2795-2802, 42.

Di Colo, Giacomo, Controlled Drug Release From Implantable Matrices Based on Hydrophobic Polymers, Biomaterials, 1992, 850-856, 13(12).

Dick et al, Macular edema, Retina, Third Edition, 2001, 967-981, Chapter 57.

Dinning, W.J., Intermediate Uveitis: History, Terminology, Definition Pars Planitis: Systemic Disease Associations, Dev Ophthalmol. Basel, Karger, 1992, 3-8, 23.

Dohlman et al, Treatment of Corneal Edema With a Buried Implant, Tr. Am. Acad. Opth. & Otol., 1965, 267-280.

Druilhe et al, Glucocorticoid-induced apoptosis in human eosinophils: Mechanisms of action, Apoptosis, 2003, 181-495, 8.

Duvvuri, Sridhar et al, Drug Delivery to the Retina: Challenges and Opportunities, Expert Opin Biol Ther, 2003, 45-56, 3(1).

Enyedi, Laura et al, An Intravitreal Device Providing Sustained Release of Cyclosporins and Dexamethason, Current Eye Research, 1996, 549-557.

Enzmann, V. et al, Immunological Problems of Transplantation into the Subretinal Space, Acta Anatomica, 1998, 178-183, 162.

Fatt, Irving, Flow and Diffusion in the Vitreous Body of the Eye, Bulletin of Mathematical Biology, 1975, 85-90, 37.

Fekrat, Sharon et al, The Central Vein Occlusion Study (CVOS), Clinical Trial sin Ophthalmology: A Summary and Practice Guide, 1998, 129-143, Chapter 8.

Foster, R.E. et al, Multidrug Biodegradable Polymer Implant in the Porcine PVR Model, IOVS, Abstract S196, Feb. 15, 1996, 917-9:45 am, vol. 37(3).

Frank, Robert, Etiologic mechanisms in diabetic retinopathy, Retina, 3rd Edition, 2001, 1259-1294, Chapter 71.

Friedrich, Stuart et al, Finite Element Modeling of Drug Distribution in the Vitreous Humor of the Rabbit Eye, Annals of Biomedical Engineering, 1997, 303-314, 25.

Gershon Berkson, et al., Body-Rocking and Other Habits of College Students and Persons with Mental Retardation, American Journal on Mental Retardation, 1999, 107-116, 104 (2).

Gilles, Mark et al, Safety of an Intravitreal Injection of Triamcinolone, Archives of Ophthalmology, Mar. 2004, 316-340, vol. 122.

Giuseppe Brisinda, et al., A Comparison of Injection of Botulinum Toxin and Topical Nitroglycerin Ointment for the treatment of Chronic Anal Fissure, The New England Journal of Medicine, Jul. 8, 1999, 65-69, 341 (2), US.

Goldberg, Ivan, Drugs for Glaucoma, Australian Prescriber, 2002, 142-146, 25(6).

Goodman and Gilman, Table of Contents, The Pharmacological Basis of Therapeutics, 1996, 10 pages, Ninth Edition.

Gould, Lisa et al, Fifty:Fifty Poly (DL Glycolic Acid-Lactic Acid) Copolymer as a Drug Delivery System for 5-Fluorouracil: A Histopathological Evaluation, Canadian Journal of Ophthalmol, 1994, 168-171, US.

Greenfield, Robert et al, Evaluation in Vitro of Adriamycin Immunoconjugates Synthesized Using an Acid-sensitve Hydrazone Linker, Cancer Research, 1990, 6600-6607, 50.

Guan, D. et al, The Therapeutic Window of Cyclosporine in Chinese Recipients of Renal Transplantation, Transplantation Proceedings, Feb. 1995, 850-851, 27(1).

Hainsworth, Dean et al, Sustained Release Intravitreal Dexamethasone, Journal of Ocular Pharmacology and Therapeutics, 1996, 57-63, 12-1.

Hari, Pankaj et al, Pulse Corticosteroid Therapy with Methylprednisolone or Dexamethasone, Indian J Pediatr, 1998, 557-560, 65.

Haynes, Jr., Adrenocorticotropic Hormone; Adrenocortical Steroids and their Synthetic Analogs; Inhibitors of the Synthesis and Actions of Adrenocortical Hormones, Goodman and Gilman's: The Pharmacological Basis of Therapeutics, 1990, 1431-1462, Chapter 60.

Haynes, Robert Jr, Adrenocorticotropic Hormone; Adrenocortical Steroids and Their Synthetic Analogs; Inhibitors of the Synthesis and Actions of Adrenocotical Hormones, The Pharmacological Basis of Therapeutics, 1990, 1431-1462, 8th Edition.

Hayreh, Sohan, Posterior Drainage of the Intraocular Fluid from the Vitreous, Exp. Eye. Res., 1966, 123-144, 5.

Heller, J. et al, Poly (ortho ester) biodegradable polymer systems, Methods in Enzymology, 1985, 422-436, 112.

Heller, J. et al, Poly(Ortho Esters), Biopolymers I, 1993, 41-92.

Heller, J., Hydrogels in Medicine and Pharmacy, N.A. Peppes ed., 1987, 137-149.

Heller, Jorge, Biodegradable Polymers in Controlled Drug Delivery, Critical Reviews in Therapeutic Drug Carrier Systems, 1987, 39-90, 1 (1).

Hirano, Toshihiko, Clinical Significance of Glucocorticoid Pharmacodynamics Assessed by Antilymphocyte Actions in Kidney Transplantation, Transplantation, May 1994, 1341-1348, 57(9).

Hockel, M. et al, Prevention of Peritoneal Adhesions in the Rat with Sustained Intraperitoneal Dexamethasone Delivered by a Novel Therapeutic System, Annales Chirugiae et Gynaecologiae, 1987, 306-313, 76.

Indu Bala, PLGA Nanoparticles in Drug Delivery: The State of the Art, Critical Reviews in Therapeutic Drug Carrier Systems, 2004, 387-422, 21 (5), US.

Inoue, Makoto et al, Vitreous Concentrations of Triamcinolone Acetonide in Human Eyes After Intravitreal or Subtenon Injection, Brief Reports, American Journal of Ophthalmology, 2004, 1046-1048, 138.

Jackanicz, Theodore et al, Polyactic Acid as a Biodegradable Carrier for Contraceptive Steroids, Contraception, 1973, 227-235, 8-3.

Jaffe, Glenn et al, Dexamethasone Sustained Drug Delivery Implant for the Treatment of Severe Uveitis, Retina, Brief Reports, 2000, 402-403, 20(4).

Jaffe, Glenn et al, Safety and Pharmcokinetics of an Intraocular Fluocinolone Acetonide Sustained Delivery Device, Invest. Ophth. & Visual Science, Oct. 2000, 3569-3575, 41(11).

Jaffe, Glenn et al, Safety, Efficacy and Pharmacokinetics of an Intravitreal Fluocinolone Sustained Drug Delivery System, Invest. Ophth. & Visual Science, Mar 1999, Abstract No. 5195-10:45, 40(4); 5988.

Jampel, Henry et al, Glaucoma Filtration Surgery in Monkeys Using 5-Fluorouridine in Polyanhydride Disks, Arch Ophthalmol, Mar. 1990, 430-435, 108.

Jankovic, Joseph, Botulinum Toxin in the Treatment of Tics Associated with Tourette's Syndrome, Neurology, 1993, 589P, 43(4).

Jay, Walter et al, Intravitreal Ceftazidime in a Rabbit Model: Dose- and Time-Dependent Toxicity and Pharmacokinetic Analysis, J. Ocular Pharmacology, 1987, 257-262, 3(3).

(56) References Cited

OTHER PUBLICATIONS

Jellinek, Derek et al, Inhibition of Receptor Binding by High-Affinity RNA Ligands to Vascular Endothelial Growth Factor, Biochemistry, 1994, 10450-10456, 33.

Jennings, Tom et al, Posterior Sub-Tenon's Injections of Corticosteroids in Uveitis Patients with Cystoid Macular Edema, Jpn J. Ophthalmol, 1988, 385-391, 32.

Jeong, Ji Hoon et al, Novel Intracellular Delivery System of Antisense Oligonucleotide by Self Assembled Hybrid Micelles Composed of DNA/PEG Conjugate and Cationic Fusogenic Peptide, Biconjugate Chem., 2003, 473-479, 14.

Johnson, F. et al, A Simple Method of Measuring Aqueous Humor Flow With Intravitreal Fluoresceinated Dextrans, Exp. Eye Res., Dec. 1984, 791-805, 39.

Jonas, J.B. et al, Intraocular pressure after intravitreal Injection of triamcinolone acetonide, British Journal of Ophthalmology, 2003, 24-27, 87.

Kane, Anne et al, Intravitreal Injection of Gentamicin in Rabbits, Investigative Ophthalmology & Visual Science, May 1981, 593-597, 20.

Kang, Se Woong et al, Macular Grid Photocoagulation After Intravitreal, Arch Ophthalmol, May 2006, 653-658, 124.

Kendall, Richard et al, Inhibition of Vascular Endothelial Cell Growth Factor Activity by an Endogenously Encoded Soluble Receptor, Proc. Natl. Acad. Sci., Nov. 1993, 10705-10709, 90.

Kher, V. et al, Low-Dose Dexamethasone—An Alternative Therapy for Acute Renal Allograft Rejection, Transplantation Proceedings, Oct. 1992, 1725, 24(5).

Kim, Jin et al, Inhibition of Vascular Endothelial Growth Factor-Induced Angiogenesis Suppresses Tumour Growth in Vivo, Nature, Apr. 29, 1993, 841-844, 362(6423).

Kimura, Hideya et al, Biodegradable Polymers for Ocular Drug Delivery, Ophthalmologica, 2001, 143-155, 215.

Kinsella, J.L. et al, Protein Kinase C Regulates Endothelial Cell Tube Formation on Basement Membrane Matrix, Matrigel, Experimental Cell Research, 1992, 56-62, 199.

Kochinke, F. et al, Biodegradable Drug Delivery System for Uveitis Treatment, Investigative Ophthalmology & Visual Science, Feb. 15, 1996, 186-B98, 37(3).

Kralinger, Martina et al, Slow Release of Acetylsalicyclic Acid by Intravitreal Silicone Oil, Retina, 21(5), 513-520, 2001.

Kunou, Noriuki et al., Biodegradable Scleral Implant for Controlled Intraocular Delivery of Betamethasone Phospate, Journal of Biomedical Materials Research, 2000, 635-641, 51 (4), US.

Kwak, Hyung Woo et al, Evaluation of the Retinal Toxicity and Pharmacokinetics of Dexamethasone After Intravitreal Injection, Arch. Ophthalmol, 1992, 259-66, 110.

Laurent, Ulla et al, Turnover of Hyaluronate in the Aqueous Humor and Vitreous Body of the Rabbit, Exp. Eye Res., 1983, 493-504, 36.

Lee, David et al, Complications of Subconjunctival 5-Fluorouracil Following Glaucoma Filtering Surgery, Ophthalmic Surgery, Mar. 1987, 187-190, 18(3).

Lee, David et al, Glaucoma Filtration Surgery in Rabbits Using Bioerodible Polymers and 5-Fluorouacil, Ophthalmol, Dec. 1987, 1523-1530, 94-12.

Lee, David et al, The Use of Bioerodible Polymers and 5-Fluorouracils in Glaucoma Filtration Surgery, Ophthalmology & Visual Science, Nov. 1988, 1692-1697, 29-11.

Lee, KY et al, Dexamethasone Posterior Segment Drug Delivery System for Treatment of Severe Uveitis, American Uveitis Society, 1999, 36-9:48 pm, Abstract 9.

Lee, Vincent et al, Drug Delivery to the posterior segment, Retina, 1989, 483-493, Chapter 25.

Leopold, Irving et al, Nonsteroidal and steroidal anti-inflammatory agents, Surgical Pharmacology of the Eye, 1985, 83-133.

Liesegang, Thomas et al, Basic and Clinical Science Course: Intraocular Inflammation and Uveitis, American Academy of Ophthalmology, 2003, 21 Pages, Section 9.

Marcon, Italo, A double-masked comparison of betaxolol and levobunolol for the treatment of primary open-angle glaucoma, Arq.Bras. Oftal., 1990, 27-32, 53(1).

Mariani, M. et al., Inhibition of Angiogenesis by FCE 26806, A Potent Tyrosine Kinase Inhibitor, Proceedings of the American Association for Cancer Research, Mar. 1994, Abstract 2268, 35.

Masurhiro Kodama, et al, Effects of a New Dexamethasone-Delivery System (Surodex) On Experimental Intraocular Imflammation Models, Graefe's Archice for Clinical and Expiremental Ophthalmology, 2003, 927-933, 241, US.

Mathebula, SD, A Review of Pharmacological Therapy for Glaucoma, The South African Optometrist, Sep. 2005, 89-96, 64(3).

Maurice et al, Chapter 2: Ocular Pharmacokinetics, Handbook of Experimental Pharmacology, 1984, 19-116, vol. 69.

Maurice, D.M., The Exchange of Sodium Between the Vitreous Body and the Blood and Aqueous Humor, J. Physiol., 1957, 110-125, 137.

Maurice, David, Flow of Water Between Aqueous and Vitreous Compartments in the Rabbit Eye, Am. J. Physiol., 1987, F104-F108.

Maurice, David, Micropharmaceutics of the Eye, Ocular Inflammation Ther., 1983, 97-102, 1.

Meadows, D.L. et al, Ocular Drug Delivery with Subconjunctival Implants, Proceedings of the 21st International Symposium on Controlled Release of Bioactive Materials, 1994, 593-594, 21.

Migita, Kryoshi et al, Apoptosis Induction in Human Peripheral Blood T Lymphocytes by High-Dose Steroid Therapy, Transplantation, Feb. 1997, 583-587, 63(4).

Miller, Robert et al, Degradation Rates of Oral Resorbable Implants (Polyactates and Polyglycolates): Rate Modification with Changes in PLA/PGA Copolymer Ratios, J. Biomed Materials Res, 1977, 711-719, 11.

Mittal, R. et al, Treatment of Acute Rejection in Live Related Renal Allograft Recipients: A Comparison of Three Different Protocols, Nephron., 1977, 186-189, 77.

Molfino, F. et al, IOP-lowering effect of dorzolamide 2% versus brimonidine tartrate 02%. A Prospective Randomized Cross Over Study, Investigative Ophthalmology & Visual Science, Mar. 1998, Abstract 2204-B61, 39(4); S481.

Morita, Yasushi et al, Polymer Blend Implant for Ocular Delivery of Fluorometholone, Biol. Pharm. Bull., 1998, 72-75, 21(2).

Morita, Yasushi et al., Intravitreous Delivery of Dexamethasone Sodium m-Sulfobenzoate from Poly (DL-Lactic Acid) Implants, Biological and Pharmaceutical Bulletin, 1998, 188-190, 21 (2), US.

Moseley, H. et al, Routes of Clearance of Radioactive Water From the Rabbit Vitreous, British Journal of Ophthalmology, 1984, 145-151, 68.

Nakamura, Osamu et al, Inhibition of neovascularization and tumor growth by dexamethasone, Medical Book, Jan. 1992, 37-41—Abstract in English, 44(1).

Nauck, Markus et al, Corticosteroids inhibit the expression of the vascular endothelial growth factor gene in human vascular smooth muscle cells, European Journal of Pharmacology, 1998, 309-315, 341.

Nauck, Markus et al, Induction of vascular endothelial growth factor by platelet-activating factor and platelet-derived growth factor is downregulated by corticosteroids, American Journal of Respiratory Cell and Molecular Biology, 1997, 398-406, 16.

Nilsson, Siv et al, PGF2α Increases Uveoscleral Outlow, Investigative Ophthalmology & Visual Science, Mar. 1987, ARVO Abstract 9-6:00, 28(3)284.

Ogden, Thomas et al, Basic Science and Inherited Retinal Disease, Retina Second Edition, 1994, Table of Contents Only (9 Pages), 1.

Ohtori, Akira et al, In vivo/in vitro Correlation of intravitreal Delivery of Drugs with the Help of Computer Simulation, Biol. Pharm. Bull., 1994, 283-290, 17(2).

Olga Weijtens, et al., Intraocular Penetration and Systemic Absorprion After Topical Applications of Dexamethasone Disodium Phosphate, Ophthalmology, 2002, 1887-1891, 109, US.

Olsen, Timothy et al, Human Scleral Permeability: Effects of Age, Cryotherapy, Transcleral Diode Laser, and Surgical Thinning, Invest. Ophthalmol. Vis. Sci., 1995, 1893-1903, 36.

(56) References Cited

OTHER PUBLICATIONS

Oplinger, Nancy et al, A Comparison of Corneal Autografts with Homografts, Ophthalmic Surgery and Lasers, Apr. 1998, 305-308, 29.
Orth, David, The Branch Vein Occlusion Study, Clinical Trials in Ophthalmology, A summary and practice guide, 1998, 113-127, Chapter 7.
Park, Tae Gwan et al, A New Preparation Method for Protein Loaded Poly (D, L-lactic-co-glycolic acid) Microspheres and Protein Release Mechanism Study, Journal of Controlled Release, 1998, 181-191, 55.
Patel, Niraj et al, Indications for and Outcomes of Repeat Penetrating Keratoplasty, Ophthalmology, Apr. 2000, 719-724, 107(4).
Pe'er et al, Vascular endothelial growth factor Upregulation in Human Central Retinal Vein Occlusion, Ophthalmology, 1998, 412-416, 105.
Pearson, Andrew et al, Clearance and Distribution of Ciprofloxacin After Intravitreal Injection, Retina, 1993, 328-330, 13.
Peyman, Gholam et al, A Technique for Retinal Pigment Epithelium Transplantation for Age-Related Macular Degeneration Secondary to Extensive Subfoveal Scarring, Ophthalmic Surgery, 1991, 102-108, 22(2).
Peyman, Gholam et al, Bacterial Endophthalmitis, Archives of Ophthalmology, May 1974, 416-418, 91.
Pinar, Intermediate Uveitis, Case Presentation, Immunology and Uveitis Service, Massachusetts Eye and Ear Infirmary, Feb. 3, 2005, 8 pages, www.uveitis.org/medical/articles/case/imede.html.
Plowman, Gregory et al, Receptor Tyrosine Kinases as Targets for Drug Intervention, Drug News & Perspectives, Aug. 1994, 334-339, 7(6).
Rahil, Jubrail et al, Reactivity and Mechanism of Hydrolysis of Phosphonamides, Journal of the American Chemical Society, 1981, 1723-1734, 103.
Rao et al, Mechanisms of Immune Effector Reactivity, Basic and Clinical Science Course(San Francisco: American Academy of Ophthalmology, 2000-2001, 40-176, 9, Chapter IV.
Rao, Venkateswara et al, Successful renal transplantation in a Patient With Anaphylactic Reaction to Solu-Medrol (Methylprednisolone Sodium Succinate, The American Journal of Medicine, 1982, 161-163, 72(1).
Remington, Table of Contents Only, the Science and Pharmacy, 1995, 4 Pages, 19th Edition.
Renfro, Lisa et al, Ocular Effects of Topical and Systemic Steroids, Dermatologic Clinics, 1992, 505-512, 10.
Riordan-Eva et al, Orbital floor steroid injections in the treatment of uveitis, Eye, 1994, 66-69, 8(1).
Robin, Jeffrey et al, The Histiopathology of Corneal Neovascularization, Archives of Ophthalmology, 1985, 284-287, 103(2).
Roff, W.J. et al, Permeability, Handbook of Common Polymers, 1971, 554-558, Section 64.
Rootman, D.S. et al, Toxicity and Pharmcokinetics of Intravitreally Injected Ciprofloxacin in Rabbit Eyes, Can. J. Ophthalmol, Oct. 1992, 277-282, 27(6).
Rupert R.A. Bourne, et al., Effects of Cataract Surgery on the Corneal Endothelium, Modern Phacoemulsification Compared With Exrtracapsular Cataract Surgery, Opthalmology 2004, Apr. 2004, 679-685, 111 (4), Elsevier, US.
Sasaki, Hitoshi et al, Drug Absorption Behavior after Periocular Injections, Biol. Pharm. Bull., 1999, 956-960, 22 (9).
Schimmer, Bernard et al, Adrenocorticotropic Hormone; Adrenocortical Steroids and their Synthetic Analogs; Inhibitors of the Synthesis and Actions of Adrenocortical Hormones, The Pharmacological Basis of Therapeutics, 2001, 1649-1677, 10th Edition.
Schindler, Schindler et al, The Clearance of Intravitreal Triamcinolone Acetonide, American Journal of Ophthalmology, Apr. 1982, 415-417, 93(4).
Scholes, Gary et al, Clearance of Triamcinolone From Vitreous, Arch Ophthalmol, 1985, 1567-1569, 103(10).

Schwartz, Bernard, The Response of Ocular Pressure to Corticosteroids, Ophthamol. Clin. North Am., 1966, 929-989, 6.
Shields, Bruce, Glaucoma Filtering Procedures, A Study Guide for Glaucoma, 1982, 453-476, Chapter 31.
Siebold, Earlene et al, Esterified Prostaglandin Shows 'Potent' Promise, Ocular Surgery News, Feb. 1, 1989, pp. 3, 59, 7 (3).
Skalka, Harold et al, Effect of Corticosteroids on Cataract Formation, Arch. Ophthalmol, 1980, 1773-1777, 98.
Smith, Thomas et al, Sustained-Release Subconjunctival 5-Fluorouracil, Ophthalmic Surgery and Laser, Sep. 1996, 763-767, 27-9.
Starr, Michael, Further Studies on the Effects of Prostagladin on Intraocular Pressure in the Rabbit, Exp. Eye Res., 1971, 170-177, 11.
Stewart, William et al, Washout periods for brimonidine 0.2% and Latanoprost 0.005%, American Journal of Ophthalmology, Jun. 2001, 798-799, 131(1).
Taba, K.E. et al, Intravitreal sustained release Fluocinolone Implant Inhibits Experimental Coroidal Neovascularization, IOVS, Monday 8:30-1015 am; Angiogenesis Paper Presentation, Room 305, Mar. 15, 1999, KP009045225, S172-9:20-9:00, Abstract one page, 40(4).
Takano, S. et al, Inhibition of Angiogenesis by a Novel Diaminoanthraquinone that Inhibits Protein Kinase C, Protein Kinases, Wednesday 1993, 2072-2077, Abstract 2 pages, 358a, 2076.
Tan, D.T.H., Randomized Clinical Trial of a New Dexamethasone Delivery System (Surodex) for Treatment of Post-Cataract Surgery Inflammation, Ophthalmology, Feb. 1999, 223-231, 106 (2), US.
Tan, Donald et al, Randomized Clinical Trial of a New Dexamethasone Delivery System (Surodex) for Treatment of Post-Cataract Surgery Inflammation, Ophthalmology, Feb. 1999, 223-231, 106 (2).
Tennant, Jerald, Cystoid Maculopathy, 125 Prostaglandins in Ophthalmology, 1978, Current Concepts in cataract surgery selected proceedings of the filth biennial Cataract Surgical Congress, 360-362, Section Three.
The National Formulary, United States Pharmacopeia, USP24, 2000, 1941-1951, 19.
Theng et al, Pharmacokinetic and Toxicity Study of an Intraocular Cyclosporine DDS in the Anterior Segment of Rabbit Eyes, Investigative Ophthalmology & Visual Science, Nov. 2003, 4895-4899, 44(11).
Theng, Julian et al, Pharmacokinetic and Toxicity Study of Intraocular Cyclosporine DDS in the Anterior Segment of Rabbit Eyes, Investigative Ophthalmology & Visual Science, Nov. 2003, 4895-4899, 44 (11), US.
Tourette Syndrome and Other Tic Disorders, 3 Pages, Retrieved from http://www.geocities.com/Hollywood/2219/diag.html?20077 on Jun. 7, 2007.
Tracy, M.A. et al, Factors Affecting the Degradation Rate of Poly(actide-co-glycolide) Microspheres in Vivo and in Vitro, Biomaterials, 1999, 1057-1062, 20.
Tsubota, Ocular surface management in corneal transplantation, Japanese Journal of Ophthalmology, 1999, 502-508, 43.
Turcotte et al, Rejection Crises in Human Renal Transplant Recipients, Control with High Dose Methylprednisolone Therapy, Archives of Surgery, 1972, 230-234, 105(1).
U.S. Appl. No. 07/386,835, filed Jul. 27, 1989.
U.S. Appl. No. 07/357,394, filed May 25, 1989.
U.S. Appl. No. 10/340,237, filed Jan. 9, 2003.
U.S. Board of Patent Appeals & Interferences, Decision on Appeal No. 2009-013914 in U.S. Appl. No. 10/340,237, (Ex Pane Nivaggioli et al), mailed Sep. 21, 2010, 19 pages.
U.S. Appl. No. 10/387,355, filed Apr. 30, 2004.
U.S. Appl. No. 10/671,816, filed Sep. 25, 2003.
U.S. Appl. No. 10/820,563, filed Apr. 8, 2004.
U.S. Appl. No. 11/944,337, filed Nov. 21, 2007.
U.S. Appl. No. 13/224,041, filed Sep. 1, 2011.
U.S. Appl. No. 13/296,957, filed Nov. 15, 2001.
U.S. Appl. No. 13/494,591, filed Jun. 12, 2012.
U.S. Appl. No. 13/797,230, filed Mar. 12, 2013.
U.S. Appl. No. 60/587,092, filed Jul. 12, 2004.

(56) References Cited

OTHER PUBLICATIONS

United States Pharmacopeia, The National Formulary, USP23, 1995, 1790-1798, 18.
USPTO Non-Final Office Action mailed Jan. 28, 2013 in U.S. Appl. No. 13/296,957, 5 pages.
USPTO Office Action in U.S. Appl. No. 12/113,434, 16 pages, mailed Dec. 16, 2008.
Wadood, Azfar et al, Safety and Efficacy of a Dexamethasone Anterior Segment Delivery System in Patients After Phacoemulsification, Journal of Cataract and Refractive Surgery, Apr. 2004, 761-768, 30.
Watson, Peter et al, A Six-month, randomized, double-masked study comparing latanoprost with Timolol in Open-angle glaucoma and ocular hypertension, The Journal of the American Academy of Ophthalmology, 1996, 126-137, 103(1).
Weisbecker, Clement et al, Physicians' desk reference for Ophthalmology, 27th Edition, 1999, 7-8 and 278-279.
Wingate, RJB et al, Intravitreal Triamcinolone and Elevated Intraocular Pressure, Australian and New Zealand Journal of Ophthalmology, Dec. 1999, 431-432, 27.
Woodward, David et al, AGN 192024 (LumiganR): A Synthetic Prostamide Analog that Lowers Primate Intraocular Pressure by Virtue of Its Inherent Pharmacological Activity, ARVO, 2002, 1 page (Abstract), 43.
Woodward, David et al, The Pharmacology of Bimatoprost (LumiganTM), Sury Ophthalmol, 2001, S337-S345, Suppl 4.
Wright, Paul et al, Inhibition of Angiogenesis in Vitro and in Ovo with an inhibitor of Cellular Protein Kinases, MDL 27032, Journal of Cellular Physiology, Sep. 1992, 448-457, 152(3).
Written Opinion by the International Preliminary Examining Authority for International Application No. PCT/ US01/21173, mailed Aug. 30, 2002, 6 pages.
Xu, Jing et al, Permeability and Diffusion in Vitreious Humor: Implications for Drug Delivery, Pharmaceutical Research, Jan. 10, 2000, 664-669, 17(6).
Zhou, Tianhong et al, Development of a Multiple-Drug Delivery Implant for Intraocular Management of Proliferative Vitreoretinopathy, Journal of Controlled Release, 1998, 281-295, 55, US.

\* cited by examiner

METHODS FOR TREATING EDEMA IN THE EYE AND INTRAOCULAR IMPLANTS FOR USE THEREFOR

CROSS-REFERENCE TO RELATED APPLICATIONS

This application is a continuation of U.S. application Ser. No. 14/481,778, filed on Sep. 9, 2014, which is a continuation of U.S. application Ser. No. 13/871,214, filed on Apr. 26, 2013, now issued as U.S. Pat. No. 8,828,446, which is a continuation of U.S. application Ser. No. 13/296,957, filed on Nov. 15, 2011, now abandoned which is a continuation of U.S. application Ser. No. 11/852,223, filed Sep. 7, 2007,now issued as U.S. Pat. No. 8,088,407, which is a divisional of U.S. application Ser. No. 11/738,409, filed Apr. 20, 2007, now issued as U.S. Pat. No. 7,625,582, which is a divisional of U.S. application Ser. No. 11/180,079, filed Jul. 11, 2005, now issued as U.S. Pat. No. 7,767,223, which is a continuation of U.S. application Ser. No. 10/744,560, filed Dec. 22, 2003, now issued as U.S. Pat. No. 7,033,605, which is a continuation of U.S. application Ser. No. 09/997,094, filed Nov. 28, 2001, now issued as U.S. Pat. No. 6,699,493, which claims the benefit of U.S. Provisional Application No. 60/250,023, filed Nov. 29, 2000 and U.S. Provisional Application No. 60/298,253, filed Jun. 12, 2001. The entire disclosure of all aforementioned U.S. Patent Applications are incorporated herein by reference.

TECHNICAL FIELD

This invention relates to the field of transplantation, in particular transplantation of components of the eye, and methods for preventing transplant rejection.

BACKGROUND ART

Certain conditions and diseases of the eye, such as corneal failure, keratoconus, corneal dystrophies, scarring, age related macular degeneration (AMD) and retinitis pigmentosa, have been treated using ocular transplant procedures such as corneal and retinal pigment epithelial (RPE) transplants. Transplant rejection is one of the problems which may arise from transplant procedures (Enzmann V et al. (1998). "Immunological problems of transplantation into the subretinal space." Acta Anat (Basel). 162(2-3): 178-83). In spite of the overall success with corneal transplants, a substantial percentage of corneal grafts experience at least one rejection episode (PCT/US97/21393).

One of the problems with present immunosuppressive drug therapy is the inability to achieve adequate intraocular drug concentrations. Systemic immunosuppression may require prolonged exposure to high plasma concentrations so that therapeutic levels can be achieved in the eye. Overall drug delivery to the eye may be poor due to the short drug plasma half-life limiting exposure into intraocular tissues. In addition, this may turn lead to numerous negative side effects.

There is a continued need for improved intraocular sustained release drug therapies for patients following ocular transplant procedures.

All references cited in this patent are incorporated herein by reference in their entirety.

DISCLOSURE OF THE INVENTION

One embodiment of the present invention provides a method for reducing or preventing transplant rejection in the eye of an individual, where the method comprises: a) performing an ocular transplant procedure; and b) implanting in the eye a bioerodible drug delivery system comprising an immunosuppressive agent and a bioerodible polymer.

Another embodiment of the invention provides a method for reducing or preventing transplant rejection in the eye of an individual, where the method comprises: a) performing an ocular transplant procedure; and b) implanting a solid body into the eye, said body comprising particles of an immunosuppressive agent entrapped within a bioerodible polymer, whereby said agent is released from the body by erosion of the polymer.

Another embodiment of the invention provides a method which includes placing in an eye of an individual a bioerodible drug delivery system, where the bioerodible drug delivery system includes an immunosuppressive agent and a bioerodible polymer; and where the eye of the individual has undergone or is undergoing an ocular transplant procedure. This method may be used to reduce or prevent transplant rejection.

Another embodiment of the invention provides a kit comprising: a) a bioerodible drug delivery system comprising an immunosuppressive agent and a bioerodible polymer, wherein the drug delivery system is designed to be implanted in the eye; and b) instructions for use. This kit may be used to reduce or prevent transplant rejection.

MODES FOR CARRYING OUT THE INVENTION

Definitions

An "ocular transplant procedure," as used herein, refers to any transplant procedure performed in the eye. Non-limiting examples of ocular transplant procedures include, but are not limited to, retinal pigment epithelium (RPE) transplant and cornea transplant. It includes autograft, allograft and xenograft transplant procedures.

"Immunosuppressive agent," "agent," "immunosuppressive drug," and "drug," are used interchangeably herein, and refer to any agent which inhibits or prevents an immune response against the transplanted tissue following a transplant procedure. Exemplary agents include, but are not limited to, dexamethasone, cyclosporin A, azathioprine, brequinar, gusperimus, 6-mercaptopurine, mizoribine, rapamycin, tacrolimus (FK-506), folic acid analogs (e.g., denopterin, edatrexate, methotrexate, piritrexim, pteropterin, Tomudex®, trimetrexate), purine analogs (e.g., cladribine, fludarabine, 6-mercaptopurine, thiamiprine, thiaguanine), pyrimidine analogs (e.g., ancitabine, azacitidine, 6-azauridine, carmofur, cytarabine, doxifluridine, emitefur, enocitabine, floxuridine, fluorouracil, gemcitabine, tegafur), fluocinolone, triaminolone, anecortave acetate, flurometholone, medrysone, and prednislone.

An "implant" and a "drug delivery system," are used interchangeably herein, and include any bioerodible device for implantation in the eye which is capable of delivering a therapeutic level of drug to the eye.

To "implant" to "place" and to "insert" are equivalent as used in this patent and mean to place an object in the desired site by any means capable of placing the object at that site.

By "therapeutic level" is meant a level of drug sufficient to prevent, inhibit, or reduce the level of transplant rejection in the eye.

The term "bioerodible polymer" refers to polymers which degrade in vivo, and wherein erosion of the polymer over time is required to achieve the agent release kinetics according to the invention. Specifically, hydrogels such as methylcellulose which act to release drug through polymer swelling are specifically excluded from the term "bioerodible polymer". The terms "bioerodible" and "biodegradable" are equivalent and are used interchangeably in this patent.

An "individual" is a vertebrate, preferably mammal, more preferably a human. Mammals include, but are not limited to, humans, rodents, sport animals and pets, such as rats, dogs, and horses.

Methods for Reducing or Preventing Transplant Rejection

Intraocular immunosuppressive drug delivery systems made of a biodegradable polymer matrix are provided which can release drug loads over various programmed time periods. When inserted into the eye these drug delivery systems provide therapeutic levels of immunosuppressive agent for reducing or preventing transplant rejection.

Accordingly, one embodiment of the present invention provides a method for reducing or preventing transplant rejection in the eye of an individual, comprising: performing an ocular transplant procedure; and implanting in the eye a bioerodible drug delivery system comprising an immunosuppressive agent and a bioerodible polymer.

In another embodiment of the invention, a method for reducing or preventing transplant rejection in the eye of an individual is provided, comprising: performing an ocular transplant procedure; and implanting a solid body into the eye, said body comprising particles of an immunosuppressive agent entrapped within a bioerodible polymer, whereby said agent is released from the body by erosion of the polymer.

Ocular transplant procedures which may be used with the methods of the invention include, but are not limited to, cornea transplant and RPE transplant. Methods for performing these transplant procedures are well known in the art. Methods for performing RPE transplants are described in, for example, U.S. Pat. Nos. 5,962,027, 6,045,791, and 5,941,250 and in *Eye Graefes Arch Clin Fxp Opthalmol* 1997 March; 235(3): 149-58; *Biochem Biophys Res Commun* 2000 Feb. 24; 268(3): 842-6; *Opthalmic Surg* 1991 February; 22(2): 102-8. Methods for performing corneal transplants are described in, for example, U.S. Pat. No. 5,755,785, and in *Eye* 1995; 9 (Pt 6 Su):6-12; *Curr Opin Opthalmol* 1992 August; 3 (4): 473-81; *Ophthalmic Surg Lasers* 1998 April; 29 (4): 305-8; *Ophthalmology* 2000 April; 107 (4): 719-24; and *Jpn J Ophthalmol* 1999 November-December; 43(6): 502-8. Exemplary methods for corneal and RPE transplantation in animal models are described in Examples 1, 4 and 5 below. In a preferred embodiment, the ocular transplant procedure is a cornea transplant. In another preferred embodiment, the ocular transplant procedure is an RPE procedure.

The drug delivery system may be implanted at various sites in the eye, depending on the size, shape and formulation of the implant, the type of transplant procedure, etc. Suitable sites include but are not limited to the anterior chamber, anterior segment, posterior chamber, posterior segment, vitreous cavity, suprachoroidal space, subconjunctiva, episcleral, intracorneal, epicorneal and sclera. In a preferred embodiment, the drug delivery system is placed in the anterior chamber of the eye. In another preferred embodiment, the drug delivery system is placed in the vitreous cavity.

The implants may be inserted into the eye by a variety of methods, including placement by forceps or by trocar following making an incision in the sclera (for example, a 2-3 mm incision) or other suitable site. In some cases, the implant may be able to be placed by trocar without making a separate incision, but instead by punching a hole directly into the eye with the trocar. The method of placement may influence the drug release kinetics. For example, implanting the device into the vitreous with a trocar may result in placement of the device deeper within the vitreous than placement by forceps, which may result in the implant being closer to the edge of the vitreous. The location of the implanted device may influence the concentration gradients of drug surrounding the device, and thus influence the release rates (e.g., a device placed closer to the edge of the vitreous may result in a slower release rate).

U.S. Pat. No. 5,869,079 further describes locations for intraocular implants and methods for insertion (see in particular col. 6-7).

In one embodiment, the implant delivers the immunosuppressive agent for at least about 5 days. In other embodiments, the implant delivers the immunosuppressive agent for at least about one week, at least about 2 weeks, at least about 3 weeks, at least about four weeks, at least about five weeks, at least about six weeks, at least about seven weeks, at least about eight weeks, at least about nine weeks, at least about 10 weeks, and at least about 12 weeks. The preferred duration of drug release may be determined by the type of transplant, the medical history of the patient, etc. In one embodiment, drug release may occur for up to 6 months, or one year, or longer. In one embodiment, more than one implant may be sequentially implanted into the vitreous in order to maintain drug concentrations for even longer periods. In one embodiment, more than one implant may be sequentially implanted into the eye in order to maintain therapeutic drug concentrations for longer periods. Co-owned U.S. patent application Ser. No. 09/693,008, titled "Methods For Treating Inflammation-Mediated Conditions of the Eye," to Wong el al. filed Oct. 20, 2000, which is expressly incorporated herein by reference in its entirety, further describes implants and methods for making the implants which can achieve and maintain particular drug concentrations for programmed extended periods of time.

The methods of the invention are preferably performed on vertebrates, preferably mammal, more preferably a human. Mammals include, but are not limited to, humans, rodents, sport animals and pets, such as rats, dogs and horses.

Implants

The formulation of the implants for use in the invention may vary according to the preferred drug release profile, the particular immunosuppressive agent used, the transplant procedure, the medical history of the patient and other factors affecting the formulation.

The implants of the invention are formulated with particles of the immunosuppressive agent associated with the bioerodible polymer matrix. In a preferred embodiment the immunosuppressive agent is entrapped within the bioerodible polymer matrix. Without being bound by theory, we hypothesize that release of the agent is achieved by erosion of the polymer followed by exposure of previously entrapped agent particles to the eye, and subsequent dissolution and release of agent. The release kinetics achieved by this form of drug release are different than that achieved through formulations which release drug through polymer swelling, such as with hydrogels such as methylcellulose. In that case, the drug is not released through polymer erosion, but through polymer swelling, which release drug as liquid diffuses through the pathways exposed. The parameters which may determine the release kinetics include the size of the drug particles, the water solubility of the drug, the ratio of drug to polymer, the method of manufacture, the surface area exposed, and the erosion rate of the polymer.

In a preferred embodiment the immunosuppressive agent is selected from the group consisting of dexamethasone, cyclosporin A, azathioprine, brequinar, gusperimus, 6-mercaptopurine, mizoribine, rapamycin, tacrolimus (FK-506), folic acid analogs (e.g., denopterin, edatrexate, methotrexate, piritrexim, pteropterin, Tomudex®, trimetrexate), purine analogs (e.g., cladribine, fludarabine, 6-mercaptopurine, thiamiprine, thiaguanine), pyrimidine analogs (e.g., ancitabine, azacitidine, 6-azauridine, carmofur, cytarabine, doxifluridine, emitefur, enocitabine, floxuridine, fluorouracil, gemcitabine, tegafur) fluocinolone, triaminolone, anecortave acetate, fluorometholone, medrysone, and prednisolone. In a preferred embodiment, the immunosuppressive agent is dexamethasone. In another preferred embodiment, the immunosuppressive agent is cyclosporin A. In another embodiment, the bioerodible implant comprises more than one immunosuppressive agent.

The implants may further comprise one or more additional therapeutic agents, such as antibiotics or antiinflammatory agents. Specific antibiotics include, but are not limited to:

Antibacterial Antibiotics:

Aminoglycosides (e.g., amikacin, apramycin, arbekacin, bambermycins, butirosin, dibekacin, dihydrostreptomycin, fortimicin(s), gentamicin, isepamicin, kanamycin, micronomicin, neomycin, neomycin undecylenate, netilmicin, paromomycin, ribostamycin, sisomicin, spectinomycin, streptomycin, tobramycin, trospectomycin), amphenicols (e.g., azidamfenicol, chloramphenicol, florfenicol, thiamphenicol), ansamycins (e.g., rifamide, rifampin, rifamycin sv, rifapentine, rifaximin), ƅ-lactams (e.g., carbacephems (e.g., loracarbef), carbapenems (e.g., biapenem, imipenem, meropenem, panipenem), cephalosporins (e.g., cefaclor, cefadroxil, cefamandole, cefatrizine, cefazedone, cefazolin, cefcapene pivoxil, cefclidin, cefdinir, cefditoren, cefepime, cefetamet, cefixime, cefmenoxime, cefodizime, cefonicid, cefoperazone, ceforanide, cefotaxime, cefotiam, cefozopran, cefpimizole, cefpiramide, cefpirome, cefpodoxime proxetil, cefprozil, cefroxadine, cefsulodin, ceftazidime, cefteram, ceftezole, ceftibuten, ceftizoxime, ceftriaxone, cefuroxime, cefuzonam, cephacetrile sodium, cephalexin, cephaloglycin, cephaloridine, cephalosporin, cephalothin, cephapirin sodium, cephradine, pivcefalexin), cephamycins (e.g., cefbuperazone, cefmetazole, cefminox, cefotetan, cefoxitin), monobactams (e.g., aztreonam, carumonam, tigemonam), oxacephems, flomoxef, moxalactam), penicillins (e.g., amdinocillin, amdinocillin pivoxil, amoxicillin, ampicillin, apalcillin, aspoxicillin, azidocillin, azlocillin, bacampicillin, benzylpenicillinic acid, benzylpenicillin sodium, carbenicillin, carindacillin, clometocillin, cloxacillin, cyclacillin, dicloxacillin, epicillin, fenbenicillin, floxacillin, hetacillin, lenampicillin, metampicillin, methicillin sodium, mezlocillin, nafcillin sodium, oxacillin, penamecillin, penethamate hydriodide, penicillin g benethamine, penicillin g benzathine, penicillin g benzhydrylamine, penicillin g calcium, penicillin g hydrabamine, penicillin g potassium, penicillin g procaine, penicillin n, penicillin o, penicillin v, penicillin v benzathine, penicillin v hydrabamine, penimepicycline, phenethicillin potassium, piperacillin, pivampicillin, propicillin, quinacillin, sulbenicillin, sultamicillin, talampicillin, temocillin, ticarcillin), other (e.g., ritipenem), lincosamides (e.g., clindamycin, lincomycin), macrolides (e.g., azithromycin, carbomycin, clarithromycin, dirithromycin, erythromycin, erythromycin acistrate, erythromycin estolate, erythromycin glucoheptonate, erythromycin lactobionate, erythromycin propionate, erythromycin stearate, josamycin, leucomycins, midecamycins, miokamycin, oleandomycin, primycin, rokitamycin, rosaramicin, roxithromycin, spiramycin, troleandomycin), polypeptides (e.g., amphomycin, bacitracin, capreomycin, colistin, enduracidin, enviomycin, fusafungine, gramicidin s, gramicidin(s), mikamycin, polymyxin, pristinamycin, ristocetin, teicoplanin, thiostrepton, tuberactinomycin, tyrocidine, tyrothricin, vancomycin, viomycin, virginiamycin, zinc bacitracin), tetracyclines (e.g., apicycline, chlortetracycline, clomocycline, demeclocycline, doxycycline, guamecycline, lymecycline, meclocycline, methacycline, minocycline, oxytetracycline, penimepicycline, pipacycline, rolitetracycline, sancycline, tetracycline), and others (e.g., cycloserine, mupirocin, tuberin).

Synthetic Antibacterials:

2,4-Diaminopyrimidines (e.g., brodimoprim, tetroxoprim, trimethoprim), nitrofurans (e.g., furaltadone, furazolium chloride, nifuradene, nifuratel, nifurfoline, nifurpirinol, nifurprazine, nifurtoinol, nitrofurantoin), quinolones and analogs (e.g., cinoxacin, ciprofloxacin, clinafloxacin, difloxacin, enoxacin, fleroxacin, flumequine, grepafloxacin, lomefloxacin, miloxacin, nadifloxacin, nalidixic acid, norfloxacin, ofloxacin, oxolinic acid, pazufloxacin, pefloxacin, pipemidic acid, piromidic acid, rosoxacin, rufloxacin, sparfloxacin, temafloxacin, tosufloxacin, trovafloxacin), sulfonamides (e.g., acetyl sulfamethoxypyrazine, benzylsulfamide, chloramine-b, chloramine-t, dichloramine t, $n^2$-formylsulfisomidine, $n^4$-ƅ-d-glucosylsulfanilamide, mafenide, 4'-(methylsulfamoyl)sulfanilanilide, noprylsulfamide, phthalylsulfacetamide, phthalylsulfathiazole, salazosulfadimidine, succinylsulfathiazole, sulfabenzamide, sulfacetamide, sulfachlorpyridazine, sulfachrysoidine, sulfacytine, sulfadiazine, sulfadicramide, sulfadimethoxine, sulfadoxine, sulfaethidole, sulfaguanidine, sulfaguanol, sulfalene, sulfaloxic acid, sulfamerazine, sulfameter, sulfamethazine, sulfamethizole, sulfamethomidine, sulfamethoxazole, sulfamethoxypyridazine, sulfametrole, sulfamidochrysoidine, sulfamoxole, sulfanilamide, 4-sulfanilamidosalicylic acid, $n^4$-sulfanilylsulfanilamide, sulfanilylurea, n-sulfanilyl-3,4-xylamide, sulfanitran, sulfaperine, sulfaphenazole, sulfaproxyline, sulfapyrazine, sulfapyridine, sulfasomizole, sulfasymazine, sulfathiazole, sulfathiourea, sulfatolamide, sulfisomidine, sulfisoxazole) sulfones (e.g., acedapsone, acediasulfone, acetosulfone sodium, dapsone, diathymosulfone, glucosulfone sodium, solasulfone, succisulfone, sulfanilic acid, p-sulfanilylbenzylamine, sulfoxone sodium, thiazolsulfone), and others (e.g., clofoctol, hexedine, methenamine, methenamine anhydromethylenecitrate, methenamine hippurate, methenamine mandelate, methenamine sulfosalicylate, nitroxoline, taurolidine, xibornol).

Antifungal Antibiotics:

Polyenes (e.g., amphotericin b, candicidin, dermostatin, filipin, fungichromin, hachimycin, hamycin, lucensomycin, mepartricin, natamycin, nystatin, pecilocin, perimycin), others (e.g., azaserine, griseofulvin, oligomycins, neomycin undecylenate, pyrrolnitrin, siccanin, tubercidin, viridin).

Synthetic Antifungals:

Allylamines (e.g., butenafine, naftifine, terbinafine), imidazoles (e.g., bifonazole, butoconazole, chlordantoin, chlormidazole, cloconazole, clotrimazole, econazole, enilconazole, fenticonazole, flutrimazole, isoconazole, ketoconazole, lanoconazole, miconazole, omoconazole, oxiconazole nitrate, sertaconazole, sulconazole, tioconazole), thiocarbamates (e.g., tolciclate, tolindate, tolnaftate), triazoles (e.g., fluconazole, itraconazole, saperconazole, terconazole) others (e.g., acrisorcin, amorolfine, biphenamine, bromosalicylchloranilide, buclosamide, calcium propionate, chlorphenesin, ciclopirox, cloxyquin, coparaffinate, diamthazole dihydrochloride, exalamide, flucytosine, halethazole, hexetidine, loflucarban, nifuratel, potassium iodide, propionic acid, pyrithione, salicylanilide, sodium propionate, sulbentine, tenonitrozole, triacetin, ujothion, undecylenic acid, zinc propionate).

Antineoplastic:

Antibiotics and analogs (e.g., aclacinomycins, actinomycin $f_1$, anthramycin, azaserine, bleomycins, cactinomycin, carubicin, carzinophilin, chromomycins, dactinomycin, daunorubicin, 6-diazo-5-oxo-L-norleucine, doxorubicin, epirubicin, idarubicin, menogaril, mitomycins, mycophenolic acid, nogalamycin, olivomycines, peplomycin, pirarubicin, plicamycin, porfiromycin, puromycin, streptonigrin, streptozocin, tubercidin, zinostatin, zorubicin), antimetabolites (e.g. folic acid analogs (e.g., denopterin, edatrexate, methotrexate, piritrexim, pteropterin, Tomudex®, trimetrexate), purine analogs (e.g., cladribine, fludarabine, 6-mercaptopurine, thiamiprine, thioguanine), pyrimidine analogs (e.g., ancitabine, azacitidine, 6-azauridine, carmofur, cytarabine, doxifluridine, emitefur, enocitabine, floxuridine, fluorouracil, gemcitabine, tagafur).

Specific Antiinflammatory Agents Include, but are not Limited to:

Steroidal Antiinflammatory Agents:

21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, and triamcinolone hexacetonide.

Non-steroidal Antiinflammatory Agents:

Aminoarylcarboxylic acid derivatives (e.g., enfenamic acid, etofenamate, flufenamic acid, isonixin, meclofenamic acid, mefenamic acid, niflumic acid, talniflumate, terofenamate, tolfenamic acid), arylacetic acid derivatives (e.g., aceclofenac, acemetacin, alclofenac, amfenac, amtolmetin guacil, bromfenac, bufexamac, cinmetacin, clopirac, diclofenac sodium, etodolac, felbinac, fenclozic acid, fentiazac, glucametacin, ibufenac, indomethacin, isofezolac, isoxepac, lonazolac, metiazinic acid, mofezolac, oxametacine, pirazolac, proglumetacin, sulindac, tiaramide, tolmetin, tropesin, zomepirac), arylbutyric acid derivatives (e.g., bumadizon, butibufen, fenbufen, xenbucin), arylcarboxylic acids (e.g., clidanac, ketorolac, tinoridine), arylpropionic acid derivatives (e.g., alminoprofen, benoxaprofen, bermoprofen, bucloxic acid, carprofen, fenoprofen, flunoxaprofen, flurbiprofen, ibuprofen, ibuproxam, indoprofen, ketoprofen, loxoprofen, naproxen, oxaprozin, piketoprolen, pirprofen, pranoprofen, protizinic acid, suprofen, tiaprofenic acid, ximoprofen, zaltoprofen), pyrazoles (e.g., difenamizole, epirizole), pyrazolones (e.g., apazone, benzpiperylon, feprazone, mofebutazone, morazone, oxyphenbutazone, phenylbutazone, pipebuzone, propyphenazone, ramifenazone, suxibuzone, thiazolinobutazone), salicylic acid derivatives (e.g., acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamide o-acetic acid, salicylsulfuric acid, salsalate, sulfasalazine), thiazinecarboxamides (e.g., ampiroxicam, droxicam, isoxicam, lornoxicam, piroxicam, tenoxicam), ε-acetamidocaproic acid, s-adenosylmethionine, 3-amino-4-hydroxybutyric acid, amixetrine, bendazac, benzydamine, ƒ-bisabolol, bucolome, difenpiramide, ditazol, emorfazone, fepradinol, guaiazulene, nabumetone, nimesulide, oxaceprol, paranyline, perisoxal, proquazone, superoxide dismutase, tenidap, and zileuton.

The immunosuppressive agent is preferably from about 10 to 90% by weight of the implant. More preferably, the agent is from about 50 to about 80%/o by weight of the implant. In a preferred embodiment, the agent comprises about 50% by weight of the implant. In a preferred embodiment, the agent comprises about 70%/% by weight of the implant.

The implants are preferably monolithic, i.e. having the immunosuppressive agent homogeneously distributed through the polymeric matrix. In this patent, by homogeneously distributed we mean that the immunosuppressive agent is distributed evenly enough that no detrimental fluctuations in rate of immunosuppressive agent release occur because of uneven distribution of the immunosuppressive agent in the polymer matrix. The selection of the polymeric composition to be employed will vary with the desired release kinetics, the location of the implant, patient tolerance, the nature of the transplant procedure and the like. Characteristics of the polymers will include biodegradability at the site of implantation, compatibility with the agent of interest, ease of encapsulation, water insolubility, and the like. Preferably, the polymeric matrix will not be fully degraded until the drug load has been released. The polymer will usually comprise at least about 10, more usually at least about 20 weight percent of the implant. In one embodiment, the implant comprises more than one polymer.

Biodegradable polymeric compositions which may be employed may be organic esters or ethers, which when degraded result in physiologically acceptable degradation products, including the monomers. Anhydrides, amides, orthoesters or the like, by themselves or in combination with other monomers, may find use. The polymers may be condensation polymers. The polymers may be cross-linked or non-cross-linked, usually not more than lightly cross-linked, generally less than 5%, usually less than 1% cross-linked. For the most part, besides carbon and hydrogen, the polymers will include oxygen and nitrogen, particularly oxygen. The oxygen may be present as oxy, e.g., hydroxy or ether, carbonyl, e.g., non-oxo-carbonyl, such as carboxylic acid ester, and the like. The nitrogen may be present as amide, cyano and amino. The biodegrable polymers set forth in Heller, Biodegrable Polymers in Controlled Drug Delivery, in: CRC Critical Reviews in Therapeutic Drug Carrier Systems, Vol. 1. CRC Press, Boca Raton, Fla. (1987), may be used.

Of particular interest are polymers of hydroxyaliphatic carboxylic acids, either homo- or copolymers, and polysaccharides. Included among the polyesters of interest are polymers of D-lactic acid, L-lactic acid, racemic lactic acid, glycolic acid, polycaprolactone, and combinations thereof. By employing the L-lactate or D-lactate, a slowly biodegrading polymer is achieved, while degradation is substantially enhanced with the racemate. Copolymers of glycolic and lactic acid are of particular interest, where the rate of biodegradation is controlled by the ratio of glycolic to lactic acid. The % of polylactic acid in the polylactic acid polyglycolic acid (PLGA) copolymer can be 0-100%, preferably about 15-85%, more preferably about 35-65%. In a particularly preferred embodiment, a 50/50 PLGA copolymer is used. The most rapidly degraded copolymer has roughly equal amounts of glycolic and lactic acid, where either homopolymer is more resistant to degradation. The ratio of glycolic acid to lactic acid will also affect the brittleness of in the implant, where a more flexible implant is desirable for larger geometries. The size of the polymer particles is preferably about 1-100 µm in diameter, more preferably about 5-50 µm in diameter, more preferably about 9-12 µm in diameter, still more preferably about 10 µm in diameter.

Among the polysaccharides of interest are calcium alginate, and functionalized celluloses, particularly carboxymethylcellulose esters characterized by being biodegradable, water insoluble, a molecular weight of about 5 kD to 500 kD, etc. In one embodiment, the implant comprises hydroxypropyl methylcellulose (HPMC).

Additionally, release modulators such as those described in U.S. Pat. No. 5,869,079 may be included in the implants. The amount of release modulator employed will be dependent on the desired release profile, the activity of the modulator, and on the release profile of the immunosuppressive agent in the absence of modulator.

Other agents may be employed in the formulation for a variety of purposes. For example, buffering agents and preservatives may be employed. Water soluble preservatives which may be employed include sodium bisulfite, sodium bisulfate, sodium thiosulfate, benzalkonium chloride, chlorobutanol, thimerosal, phenylmercuric acetate, phenylmercuric nitrate, methylparaben, polyvinyl alcohol and phenylethyl alcohol. These agents may be present in individual amounts of from about 0.001 to about 5% by weight and preferably about 0.01 to about 2%. Suitable water soluble buffering agents that may be employed are sodium carbonate, sodium borate, sodium phosphate, sodium acetate, sodium bicarbonate, etc., as approved by the FDA for the desired route of administration. These agents may be present in amounts sufficient to maintain a pH of the system of between 2 to 9 and preferably 4 to 8. As such the buffering agent may be as much as 5% on a weight to weight basis of the total composition. Electrolytes such as sodium chloride and potassium chloride may also be included in the formulation. Where the buffering agent or enhancer is hydrophilic, it may also act as a release accelerator. Hydrophilic additives act to increase the release rates through faster dissolution of the material surrounding the drug particles, which increases the surface area of the drug exposed, thereby increasing the rate of drug bioerosion. Similarly, a hydrophobic buffering agent or enhancer dissolve more slowly, slowing the exposure of drug particles, and thereby slowing the rate of drug bioerosion.

The proportions of immunosuppressive agent, polymer, and any other modifiers may be empirically determined by formulating several implants with varying proportions. A USP approved method for dissolution or release test can be used to measure the rate of release (USP 23; NF 18 (1995) pp. 1790-1798). For example, using the infinite sink method, a weighed sample of the drug delivery system is added to a measured volume of a solution containing 0.9% NaCl in water, where the solution volume will be such that the drug concentration is after release is less than 5% of saturation. The mixture is maintained at 37° C. and stirred slowly to maintain the implants in suspension. The appearance of the dissolved drug as a function of time may be followed by various methods known in the art, such as spectrophotometrically, HPLC, mass spectroscopy, etc. until the absorbance becomes constant or until greater than 90% of the drug has been released.

The release kinetics of the drug delivery systems of the invention are dependent in part on the surface area of the implants. Larger surface area exposes more polymer to the eye, causing faster erosion and dissolution of the drug particles entrapped by the polymer. The size and form of the implant can be used to control the rate of release, period of treatment, and drug concentration at the site of implantation. Larger implants will deliver a proportionately larger dose, but depending on the surface to mass ratio, may have a slower release rate. The implants may be particles, sheets, patches, plaques, films, discs, fibers, microcapsules and the like and may be of any size or shape compatible with the selected site of insertion, as long as the implants have the desired release kinetics. Preferably, the implant to be inserted is formulated as a single particle. Preferably, the implant will not migrate from the insertion site following implantation. The upper limit for the implant size will be determined by factors such as the desired release kinetics, location of the implant in the eye, toleration for the implant, size limitations on insertion, ease of handling, etc. For example, the vitreous chamber is able to accommodate relatively large implants of varying geometries, having diameters of 1 to 3 mm. In a preferred embodiment, the implant is a cylindrical pellet (e.g., rod) with dimensions of about 2 mm×0.75 mm diameter. In another preferred embodiment, the implant is a cylindrical pellet (e.g., rod) with dimensions of about 1 mm×380 µm diameter. The implants will also preferably be at least somewhat flexible so as to facilitate both insertion of the implant in the eye and accommodation of the implant. The total weight of the implant is preferably about 50-5000 µg, more preferably about 100-1000 µg. In one embodiment, the implant is about 500 µg. In a particularly preferred embodiment, the implant is about 1000 µg. In another particularly preferred embodiment, the implant is about 120 µg. U.S. Pat. No. 5,869,079 further describes preferred implant sizes for particular regions of the eye, as well as preferred sizes for particular implant shapes.

In a preferred embodiment, a solid bioerodible implant for reducing or preventing transplant rejection in the eye is provided, comprising about 50% by weight of dexamethasone, about 15% by weight of hydroxypropyl methylcellulose (HPMC) and about 35% by weight of polylactic polyglycolic acid (PLGA).

In another preferred embodiment, a solid bioerodible implant for reducing or preventing transplant rejection in the eye is provided, comprising about 70% by weight of dexamethasone and about 30% by weight of polylactic polyglycolic acid (PLGA).

In another preferred embodiment, a solid bioerodible implant for reducing or preventing transplant rejection in the eye is provided, comprising about 50% by weight of dexamethasone and about 50% by weight of polylactic polyglycolic acid (PLGA).

The preferred supplier of PLGA is Boehringer Ingelheim and the preferred PLGA products are Resomer RG 502 and Resomer RG 502H.

In a preferred embodiment, the solid bioerodible implant includes about 50% by weight of dexamethasone, about 15% by weight of hydroxypropyl methylcellulose (HPMC) and about 35% by weight of Resomer RG 502H PLGA.

In a preferred embodiment, the solid bioerodible implant includes about 60% by weight of dexamethasone, about 30% by weight of Resomer RG 502H PLGA, and about 10% by weight of Resomer RG 502 PLGA.

Methods for Making the Implants

Various techniques may be employed to produce the implants. Useful techniques include phase separation methods, interfacial methods, extrusion methods, compression methods, molding methods, injection molding methods, heat press methods and the like.

Choice of the technique and manipulation of the technique parameters employed to produce the implants can influence the release rates of the drug. Room temperature compression methods result in an implant with discrete microparticles of drug and polymer interspersed. Extrusion methods result in implants with a progressively more homogenous dispersion of the drug within the polymer, as the production temperature is increased. When using extrusion methods, the polymer and drug are chosen to as to be stable at the temperatures required for manufacturing, usually at least about 85° C. Extrusion methods use temperatures of about 25° C. to about 150° C., more preferably about 65° C. to about 130° C. Generally, compression methods yield implants with faster release rates than extrusion methods, and higher temperatures yield implants with slower release rates.

In a preferred embodiment, compression methods are used to produce the implants of the invention. Preferably, compression methods use pressures of 50-150 psi, more preferably about 70-80 psi, even more preferably about 76 psi, and use temperatures of about 0° C. to about 115° C., more preferably about 25° C. In another preferred embodiment, extrusion methods are used. Preferably, implants produced by extrusion methods are heated to a temperature range of about 60° C. to about 150° C. for drug/polymer mixing, preferably about 85° C., preferably about 130° C., for a time period of about 0 to 1 hour, 0 to 30 minutes, 5-15 minutes, preferably about 10 minutes, preferably about 0 to 5 min, preferably about 1 hour. Preferably, the implants are then extruded at a temperature of about 60° C. to about 130° C., preferably about 95° C., preferably about 85° C., preferably about 75° C.

U.S. Pat. No. 4,997,652 further describes suitable methods for making the implants of the invention, and is herein incorporated by reference in its entirety.

Kit for the Administration of the Implants

In another aspect of the invention, a kit for treating or preventing transplant rejection in the eye is provided, comprising a bioerodible drug delivery system comprising an immunosuppressive agent and a bioerodible polymer, wherein the drug delivery system is designed to be implanted in the eye. The kit may also include instructions for use.

The bioerodible drug delivery systems as described herein are suitable for use in the kits of the invention. In a preferred embodiment, the immunosuppressive agent is dexamethasone.

The invention is further described by the following non-limiting examples.

EXAMPLES

Example 1

Effect of Dexamethasone Implant in Animal Penetrating Keratoplasty Model

The objective of this study was to determine the efficacy of sustained release intraocular dexamethasone implanted in the anterior chamber of the rat eye at the end of cornea transplant surgery and compare it with local eye drop therapy. The approximately 120 μg dexamethasone implant contained about 15% HPMC, 35% PLGA and 50% dexamethasone, and was prepared and tested in vitro as described in U.S. Pat. No. 5,869,079 (See Example 1), which is specifically incorporated herein by reference in its entirety.

In order to create a very high risk of cornea rejection, a xenograft model was chosen. Mouse cornea from 12 mice of either sex were used as donor tissues for rat.

Eighteen rats of either sex were used in the study. They were divided into 3 groups. Group #1—6 animals received treatment with the dexamethasone implant, Group #2—received treatment with topical steroid and Group #3—control group (without any treatment). Animals were followed up to 8 weeks. After euthanasia eyes were sent for histopathology examination.

TABLE 1

Study design

| Animal # | Group # | Eye | Treatment |
|---|---|---|---|
| 1 | 1 | OD | Dex implant |
| 2 | 1 | " | " |
| 3 | 1 | " | " |
| 4 | 1 | " | " |
| 5 | 1 | " | " |
| 6 | 1 | " | " |
| 7 | 2 | " | Dex eye drops |
| 8 | 2 | " | " |
| 9 | 2 | " | " |
| 10 | 2 | " | " |
| 11 | 2 | " | " |
| 12 | 2 | " | " |
| 13 | 3 | " | Control (no treatment) |
| 14 | 3 | " | " |
| 15 | 3 | " | " |
| 16 | 3 | " | " |
| 17 | 3 | " | " |
| 18 | 3 | " | " |

Supplies: 0.5% Ophthaine Solution, euthasol solution, ketamine HCl, xylazine

Animal Preparation and Surgical Procedure

Obtaining donor corneas: Each mouse was weighed and anesthetized. While under anesthesia, the ophthalmologist collected all donor cornea buttons from mice using trephine. After the procedure mice were euthanized by a lethal dose of Euthasol.

Penetrating keratoplasty (PKP): Each rat was weighed and anesthetized. Using 2.5 mm trephine an initial incision was made in the middle of cornea. The incision was finished using corneal scissors. The anterior chamber (AC) was held using balanced salt solution (BSS). The donor cornea button was attached to the host cornea with 8 interrupted sutures with 11-0 nylon. Before closing the anterior chamber, the dexamethasone implant was implanted into the AC of the first 6 animals.

All eighteen rats survived the procedure. All eyes were examined by an ophthalmologist by slit lamp and all signs of cornea rejection (neovascularization, edema, etc.) were recorded.

In group #2, all animals received 2 drops of Dexamethasone eye drops every day, until the rejection occurred.

Based on clinical observation, rejection of cornea in Group #3 (control) occurred in the first few days after surgery, and by week one 80, of donors' cornea were rejected, by week two 100%. Corneas were showing heavy neovascularization in the first few days followed by corneal edema and total rejection. Group #2 (topical Dexamethasone eye drops) had similar signs observed in this group with some delay. 20% of cornea rejection occurred by week two, 50% by week three, and 80% by week six. At the time of euthanasia (week 8) only 20% were not completely rejected.

However, in group #1, treated with the dexamethasone implant, the corneas did not show any signs of rejection (neovascularization, edema). In all eyes the corneas stayed clear. By the end of the study (week eight) the graft survival was 100%.

Histopathology examination confirmed the clinical observations. In Group #3 heavy inflammation was observed in AC, cornea endothelium, also in the stroma, and some in the epithelium. Corneas also showed edema due to destroyed endothelial cells.

In Group #2 similar findings were observed.

In Group #1, inflammation was totally suppressed by the dexamethasone implant.

The entire clinical and histological finding in this study clearly demonstrated that intraocular sustained release Dexamethasone can prevent corneal rejection in a high-risk xenograft model.

Example 2

Manufacture and in Vitro Testing of Bioerodible Dexamethasone Posterior Segment Drug Delivery System (DEX PS DDS®)

2100 mg of dexamethasone powder (Upjohn) (particle sizes less than 10 μm in diameter) were mixed with 900 mg of 50/50 polylactic acid polyglycolic acid (PLGA) (particle sizes approximately 9-12 μm in diameter) at ambient temperature. A small Teflon® tube was filled with 900-1100 μg of the above mixture, and placed directly on the die cavity. The powder was pushed out of the tubing into the die cavity with a stainless steel wire and the tube and wire were removed from the die. The powder was pressed using a tablet press (approximately 76 psi), ejected with the ejector switch, and removed with tweezers. The resulting pellet was approximately 2 mm×0.75 mm.

Release of dexamethasone from the DEX PS DDS® system was measured. One DDS was placed in a glass vial filled with receptor medium (0.9% NaCl in water). To allow for "infinite sink" conditions, the receptor medium volume was chosen so that the concentration would never exceed 5% of saturation. To minimize secondary transport phenomena, e.g. concentration polarization in the stagnant boundary layer, the glass vial was placed into a shaking water bath at 37° C. Samples were taken for HPLC analysis from the vial at defined time points. The HPLC method was as described in USP 23(1995) pp. 1791-1798. The concentration values were used to calculate the cumulative release data, as shown in Table 2.

TABLE 2

DEX PS DDS ® In vitro Release

| Day | % Total Release |
| --- | --- |
| 1 | 10.1 |
| 2 | 16.4 |
| 7 | 39.4 |
| 14 | 55.5 |
| 21 | 69.3 |
| 28 | 80.7 |
| 35 | 88.1 |

Table 2 shows an almost linear in vitro release of dexamethasone over a one month period of time.

Example 3

In Vivo Testing of DEX PS DDS® in Rabbits

One DEX PS DDS® per eye was implanted into the vitreous of four rabbits with forceps. The in vivo vitreous concentrations of dexamethasone in each of the four eyes were monitored by vitreous sampling. For example, at day 2 the concentrations measured were 0.03 μg/ml, 0.1 μg/ml, 0.33 μg/ml and 0.19 μg/ml. The concentrations in each of the four eyes were measured on days 2, 7, 21, 28 and 35; the average results are summarized in Table 3. The volume of rabbit eyes is approximately 60-70% percent that of human eyes.

TABLE 3

In vivo concentrations of dexamethasone (DDS placed with forceps)

| Day | μg/ml |
| --- | --- |
| 2 | 0.16 ± 0.13 |
| 7 | 0.15 ± 0.16 |
| 21 | 0.08 ± 0.07 |
| 28 | 0.005 ± 0.01 |
| 35 | 0.037 ± 0.03 |

The same DDS was tested in vivo in rabbits, wherein the DDS was placed to a depth of about 5-10 mm in the vitreous with trocar. The levels of dexamethasone in the vitreous are shown in Table 4.

TABLE 4

In vivo concentrations of dexamethasone (DDS placed with trocar)

| Hours | Sample ID | | | | | | | | Avg | SD |
| --- | --- | --- | --- | --- | --- | --- | --- | --- | --- | --- |
| | 5293-D | 5295 = D | 5293-S | 5295-S | 5304-D | 5306-D | 5304-S | 5306-S | | |
| | | | Sample Conc., μg/ml | | | | | | | |
| 2 | 0.56 | 3.07 | | | | | | | 1.82 | 1.77 |
| 4 | | | 5.48 | 6.95 | | | | | 6.22 | 1.04 |
| 6 | | | | | 2.08 | 5.15 | | | 3.62 | 2.17 |
| 24 | | | | | | | 2.33 | 2.69 | 2.51 | 0.25 |

TABLE 4-continued

In vivo concentrations of dexamethasone (DDS placed with trocar)

| Animal#\day | DDS wt. μg | Dex wt. μg | Dex μg/mL | | | | | |
|---|---|---|---|---|---|---|---|---|
| | | | 2 | 7 | 14 | 21 | 28 | 35 |
| 21427-D | 990 | 693 | 2.29 | | | | | |
| 21427-S | 1023 | 715.1 | 1.56 | | | | | |
| 21433-D | 804 | 562.8 | 1.2 | | | | | |
| 21433-S | 1057 | 739.9 | 0.77 | | | | | |
| 21428-D | 1003 | 702.1 | | 9.26 | | | | |
| 21428-S | 1025 | 717.5 | | 0.35 | | | | |
| 21434-D | 863 | 604.1 | | 3.31 | | | | |
| 21434-S | 1106 | 774.2 | | 0.84 | | | | |
| 21429-D | 1013 | 709.1 | | | n/a | | | |
| 21429-S | 927 | 648.9 | | | 0.19 | | | |
| 21435-D | 1104 | 772.8 | | | 0.43 | | | |
| 21435-S | 941 | 658.7 | | | 0.11 | | | |
| 21432-D | 860 | 692 | | | | 0.43 | | |
| 21432-S | 941 | 685.7 | | | | 1.72 | | |
| 21436-D | 1010 | 707 | | | | 0.31 | | |
| 21436-S | 1054 | 737.8 | | | | 0.13 | | |
| 21431-D | 996 | 697.2 | | | | | 0.52 | |
| 21431-S | 918 | 642.6 | | | | | 1.15 | |
| 21437-D | 1049 | 732.9 | | | | | 0.19 | |
| 21437-D | 1075 | 752.5 | | | | | 0.48 | |
| 21430-D | 994 | 695.8 | | | | | | 0.06 |
| 21430-S | 1086 | 760.2 | | | | | | 0.18 |
| 21438-D | 974 | 681.8 | | | | | | 0.03 |
| 21438-S | 831 | 581.7 | | | | | | 8.35 |
| Ave. | 985.17 | 694.43 | 1.46 | 3.44 | 0.24 | 0.65 | 0.59 | 2.16 |

* Unable to determine due to insufficient sample

The data indicate that the DEX PS DDS® releases dexamethasone to the vitreous in concentrations above 0.01 μg/ml for an extended period of time. Further, the data indicate that placement of the device with trocar results in much higher levels of drug release than with placement with forceps, most likely due to placement of the device deeper within the vitreous. The data at two, four, six, and 24 hours in Table 4 shows an initial spike of drug release.

Example 4

Manufacture and in Vitro Testing of 50/50 Dexamethasone/PLGA Posterior Segment Drug Delivery System 2.5 g of PLGA (particle sizes approximately 9-12 μm in diameter) were placed in a mixing vessel. The vessel was placed in the oven (130° C.) for ten minutes. 2.5 g of dexamethasone (particle sizes less than approximately 10 μm in diameter) were added to the vessel, and the vessel was returned to the oven for 10 minutes. The PLGA/dexamethasone mixture was mixed well, the blend loaded into a barrel, and 650-790 μm diameter filaments extruded. The resulting filaments were cut into lengths of approximately 0.94 and 1.87 mm for the 500 μg and 1000 μg formulations, respectively.

Release of dexamethasone from the 50/50 dexamethasone/PLGA DDS formulations were measured. One DDS was placed in a glass vial filled with receptor medium (0.9% NaCl in water). To allow for "infinite sink" conditions, the receptor medium volume was chosen so that the concentration would never exceed 5% of saturation. To minimize secondary transport phenomena, e.g. concentration polarization in the stagnant boundary layer, the glass vial was placed into a shaking water bath at 37° C. Samples were taken for HPLC analysis from the vial at defined time points. The HPLC method was as described in USP 23(1995) pp. 1791-1798. The concentration values were used to calculate the cumulative release data, as shown in Tables 5 and 6.

TABLE 5

In vitro release of 50% Dex-PS (0.5 mg formulation)

| Day | Dex μg Release/day | % Total release |
|---|---|---|
| 50% Dex PS 0.5 mg system replicate 1 | | |
| 1 | 3.00 | 1.41 |
| 7 | 1.99 | 7.93 |
| 13 | 0.90 | 13.43 |
| 20 | 1.79 | 30.21 |
| 27 | 1.54 | 49.77 |
| 34 | 1.93 | 80.52 |
| 41 | 0.24 | 85.05 |
| 48 | 0.24 | 90.38 |
| 55 | 0.10 | 93.00 |
| 62 | 0.15 | 97.44 |
| 69 | 0.07 | 99.84 |
| 76 | 0.07 | 102.25 |
| 50% Dex PS 0.5 mg system replicate 2 | | |
| 1 | 6.00 | 2.17 |
| 7 | 1.66 | 6.38 |
| 13 | 0.99 | 11.05 |
| 20 | 1.21 | 19.82 |
| 27 | 2.29 | 42.23 |
| 34 | 2.34 | 71.05 |
| 41 | 0.44 | 77.54 |
| 48 | 0.29 | 82.61 |
| 55 | 0.14 | 85.34 |
| 62 | 0.20 | 89.80 |
| 69 | 0.10 | 92.21 |
| 76 | 0.06 | 84.38 |
| 50% Dex PS 0.5 mg system replicate 3 | | |
| 1 | 5.70 | 3.27 |
| 7 | 1.11 | 7.71 |
| 13 | 0.83 | 13.83 |
| 20 | 0.05 | 14.47 |

TABLE 5-continued

In vitro release of 50% Dex-PS (0.5 mg formulation)

| Day | Dex μg Release/day | % Total release |
|---|---|---|
| 27 | 1.63 | 39.63 |
| 34 | 1.52 | 69.26 |
| 41 | 0.21 | 74.10 |
| 48 | 0.19 | 79.23 |
| 55 | 0.08 | 81.69 |
| 62 | 0.14 | 86.58 |
| 69 | 0.07 | 89.46 |
| 76 | 0.06 | 92.26 |

TABLE 6

In vitro release of 50% Dex-PS (1 mg formulation)

| Day | Dex μg Release/day | % Total release |
|---|---|---|
| *50% Dex PS 1 mg system replicate 1* | | |
| 1 | 6.90 | 1.28 |
| 7 | 3.48 | 5.78 |
| 13 | 1.93 | 10.43 |
| 20 | 3.46 | 23.22 |
| 27 | 3.74 | 41.89 |
| 34 | 3.94 | 66.83 |
| 41 | 1.79 | 80.17 |
| 48 | 1.28 | 91.49 |
| 55 | 0.21 | 93.59 |
| 62 | 0.24 | 96.39 |
| 69 | 0.11 | 97.85 |
| 76 | 0.09 | 99.11 |
| *50% Dex PS 1 mg system replicate 2* | | |
| 1 | 3.90 | 0.71 |
| 7 | 2.26 | 3.62 |
| 13 | 1.66 | 7.57 |
| 20 | 3.14 | 19.09 |
| 27 | 4.32 | 40.48 |
| 34 | 4.06 | 65.77 |
| 41 | 1.61 | 77.90 |
| 48 | 1.34 | 89.70 |
| 55 | 0.19 | 91.60 |
| 62 | 0.23 | 94.18 |
| 69 | 0.10 | 95.50 |
| 76 | 0.09 | 96.78 |
| *50% Dex PS 1 mg system replicate 3* | | |
| 1 | 4.50 | 0.91 |
| 7 | 2.16 | 3.98 |
| 13 | 1.69 | 8.42 |
| 20 | 1.25 | 13.48 |
| 27 | 3.88 | 34.67 |
| 34 | 3.53 | 58.97 |
| 41 | 1.85 | 74.28 |
| 48 | 0.88 | 82.85 |
| 55 | 0.19 | 84.94 |
| 62 | 0.26 | 88.15 |
| 69 | 0.11 | 89.75 |
| 76 | 0.10 | 91.26 |

Example 5

In Vivo Testing of 50/50 Dexamethasone/PLGA 1 mg Formulations in Rabbits

One 50/50 dexamethasone/PLGA 1 mg formulation DDS per eye was implanted into the vitreous of 6 rabbits using a trocar. The DDS was loaded into the trocar, a hole was punched through the sclera, the trocar inserted through the hole, and the trocar plunger depressed to insert the DDS into the vitreous. In vivo vitreous concentrations of dexamethasone were monitored, as shown in Table 7.

TABLE 7

In vivo vitreous concentrations of dexamethasone

| Hours | 5293-D | 5295=D | 5293-S | 5295-S | 5304-D | 5306-D | 5304-S | 5306-S | Avg | SD |
|---|---|---|---|---|---|---|---|---|---|---|
| | | | Sample Conc., μg/ml | | | | | | | |
| 2 | 1.38 | 1.69 | | | | | | | 1.54 | 0.22 |
| 4 | | | 2.16 | 0.96 | | | | | 0.47 | 0.37 |
| 6 | | | | | 0.73 | 0.21 | | | 0.47 | 0.37 |
| 24 | | | | | | | 0.57 | 0.74 | 0.66 | 0.12 |

| Animal#\day | 7 | 21 | 35 | 49 | 63 |
|---|---|---|---|---|---|
| | | | Dex μg/mL | | |
| 2953-D | 0.5 | | | 0.58 | |
| 2953-S | 0.11 | | | 0.69 | |
| 2952-D | 0.13 | | | 1.2 | |
| 2952-S | 0.12 | | | 0.55 | |
| 2946-D | | 0.19 | | | 2.55 |
| 2946-S | | *3 | | | 0.14 |
| 2949-D | | *5.44 | | | 0.28 |
| 2949-S | | 0.0248 | | | 0.01 |
| 2982-D | | | 1.087 | | |
| 2982-S | | | 0.058 | | |
| 2983-D | | | 0.018 | | |
| 2983-S | | | 0.045 | | |
| Ave. | 0.22 | 2.16 | 0.30 | 0.76 | 0.75 |

*High level was due to the surgical artifact

The data indicate that the 50/50 dexamethasone/PLGA DDS releases dexamethasone to the vitreous in concentrations above 0.01 µg/ml for an extended period of time. The data at two, four, six, and 24 hours in Table 7 shows an initial spike of drug release, due to drug which is unencapsulated by the delivery system.

Modifications of the above described modes for carrying out the invention that are obvious to those of ordinary skill in the surgical, pharmaceutical, or related arts are intended to be within the scope of the following claims.

What is claimed is:

1. A method for treating edema in an eye of an individual in need thereof, comprising: placing a bioerodible drug delivery system comprising dexamethasone and a bioerodible polymer in an eye of an individual, thereby treating edema of the eye of the individual, wherein the dexamethasone comprises about 60% by weight of the drug delivery system, based on the total weight of the drug delivery system.

2. The method of claim 1, wherein the biodegradable drug delivery system is placed in the vitreous of the eye.

3. The method of claim 1, wherein the bioerodible polymer comprises a polylactic acid polyglycolic acid (PLGA) copolymer.

4. The method of claim 1, wherein the bioerodible drug delivery system delivers the dexamethasone for at least 5 days.

5. The method of claim 1, wherein the bioerodible drug delivery system delivers the dexamethasone for at least about 3 weeks.

6. The method of claim 1, wherein the bioerodible drug delivery system delivers the dexamethasone for at least about 12 weeks.

* * * * *